United States Patent
Du

(10) Patent No.: US 10,583,068 B2
(45) Date of Patent: Mar. 10, 2020

(54) EYESIGHT-PROTECTION IMAGING APPARATUS AND EYESIGHT-PROTECTION IMAGING METHOD

(71) Applicant: Beijing Zhigu Rui Tuo Tech Co., Ltd, Beijing (CN)

(72) Inventor: Lin Du, Beijing (CN)

(73) Assignee: Beijing Zhigu Rui Tuo Tech Co., Ltd, Beijing ( * ) Notice: Subject to any disclaimer, the term of this patent is extended or adjusted under 35 U.S.C. 154(b) by 0 days.

(21) Appl. No.: 14/781,584

(22) PCT Filed: Dec. 4, 2013

(86) PCT No.: PCT/CN2013/088545
§ 371 (c)(1),
(2) Date: Sep. 30, 2015

(87) PCT Pub. No.: WO2015/024327
PCT Pub. Date: Feb. 26, 2015

(65) Prior Publication Data
US 2016/0193104 A1    Jul. 7, 2016

(30) Foreign Application Priority Data
Aug. 22, 2013    (CN) .......................... 2013 1 0370346

(51) Int. Cl.
*G02B 27/00*    (2006.01)
*A61H 5/00*    (2006.01)
(Continued)

(52) U.S. Cl.
CPC ............ *A61H 5/00* (2013.01); *A61B 3/0025* (2013.01); *A61B 3/113* (2013.01); *A61B 3/12* (2013.01);
(Continued)

(58) Field of Classification Search
CPC .......... A61H 5/00; A61B 3/14; A61B 3/0025; A61B 3/113; A61B 3/12; H04N 5/2254;
(Continued)

(56) References Cited

U.S. PATENT DOCUMENTS 4,264,154 A    4/1981 Petersen
4,572,616 A    2/1986 Kowel et al.
(Continued)

FOREIGN PATENT DOCUMENTS

CN    1372650    10/2002
CN    1470227    1/2004
(Continued)

OTHER PUBLICATIONS

International Search Report dated Mar. 6, 2014 for PCT Application No. PCT/CN2013/088540, 8 pages.
(Continued)

*Primary Examiner* — Stephone B Allen
*Assistant Examiner* — Rahman Abdur
(74) *Attorney, Agent, or Firm* — Amin, Turocy & Watson, LLP

(57) ABSTRACT

The apparatus comprises: an adjustable lens module, configured to image an object viewed by eyes an eye; an analysis and processing module, configured to determine whether time during which a change amount of a distance between a gaze point of the eye and the eye is within a set range exceeds a set threshold, and when the time exceeds the set threshold, send adjustment triggering information to a parameter generating module; the parameter generating module, configured to generate adjustment information of an imaging parameter of the adjustable lens module according to the adjustment triggering information; and a lens adjustment module, configured to adjust the imaging parameter of the adjustable lens module according to the adjustment (Continued)

information of the imaging parameter. A probability of occurrence or deterioration of a sight problem, e.g., near-sightedness, due to improper use of eyes is reduced without affecting work, study, entertainment, etc. being currently performed by a user.

51 Claims, 12 Drawing Sheets

(51) Int. Cl.
| | |
|---|---|
| G02C 7/08 | (2006.01) |
| G02B 27/01 | (2006.01) |
| A61B 3/00 | (2006.01) |
| A61B 3/113 | (2006.01) |
| A61B 3/12 | (2006.01) |
| A61B 3/14 | (2006.01) |
| G06K 9/00 | (2006.01) |
| H04N 5/225 | (2006.01) |

(52) U.S. Cl.
CPC ............ *A61B 3/14* (2013.01); *G02B 27/0093* (2013.01); *G02B 27/0172* (2013.01); *G02C 7/081* (2013.01); *G06K 9/00597* (2013.01); *H04N 5/2254* (2013.01); *G02B 2027/0138* (2013.01); *G02B 2027/0178* (2013.01); *G06T 2207/30201* (2013.01)

(58) Field of Classification Search
CPC ........... G06K 9/00597; G02B 27/0093; G02B 27/0172; G02B 2027/0178; G02B 2027/0138; G02C 7/081; G06T 2207/30201
USPC ................................ 359/291; 351/203, 209
See application file for complete search history.

(56) References Cited

U.S. PATENT DOCUMENTS

| | | | | |
|---|---|---|---|---|
| 4,973,149 | A | * | 11/1990 | Hutchinson ............ A61B 3/113 351/210 |
| 5,182,585 | A | | 1/1993 | Stoner |
| 5,537,163 | A | | 7/1996 | Ueno |
| 6,038,080 | A | | 3/2000 | Schachar |
| 6,072,443 | A | * | 6/2000 | Nasserbakht .......... G09G 3/002 345/156 |
| 6,111,597 | A | * | 8/2000 | Tabata ................ G02B 27/2264 345/8 |
| 6,151,061 | A | | 11/2000 | Tokuhashi |
| 6,152,563 | A | | 11/2000 | Hutchison et al. |
| 6,325,513 | B1 | | 12/2001 | Bergner et al. |
| 7,001,020 | B2 | | 2/2006 | Yancey et al. |
| 7,298,414 | B2 | | 11/2007 | Stavely et al. |
| 7,334,892 | B2 | | 2/2008 | Goodall et al. |
| 7,486,988 | B2 | * | 2/2009 | Goodall ............. A61B 5/04001 349/13 |
| 7,764,433 | B2 | | 7/2010 | Kam et al. |
| 7,766,479 | B2 | | 8/2010 | Ebisawa |
| 8,104,892 | B2 | | 1/2012 | Hillis et al. |
| 8,109,632 | B2 | | 2/2012 | Hillis et al. |
| 8,282,212 | B2 | | 10/2012 | Hillis et al. |
| 8,384,999 | B1 | | 2/2013 | Crosby et al. |
| 8,896,632 | B2 | | 11/2014 | MacDougall et al. |
| 2002/0101568 | A1 | | 8/2002 | Eberl et al. |
| 2002/0113943 | A1 | | 8/2002 | Trajkovic et al. |
| 2003/0043303 | A1 | | 3/2003 | Karuta et al. |
| 2003/0125638 | A1 | | 7/2003 | Husar et al. |
| 2005/0003043 | A1 | | 1/2005 | Sewal et al. |
| 2005/0014092 | A1 | | 1/2005 | Hasegawa et al. |
| 2005/0030438 | A1 | | 2/2005 | Nishioka |
| 2006/0016459 | A1 | | 1/2006 | Mcfarlane et al. |
| 2006/0103808 | A1 | | 5/2006 | Horie |
| 2006/0122530 | A1 | | 6/2006 | Goodall et al. |
| 2006/0122531 | A1 | | 6/2006 | Goodall et al. |
| 2006/0146281 | A1 | | 7/2006 | Goodall et al. |
| 2006/0164593 | A1 | | 7/2006 | Peyghambarian et al. |
| 2007/0019157 | A1 | | 1/2007 | Hillis et al. |
| 2007/0211207 | A1 | | 9/2007 | Lo et al. |
| 2008/0002262 | A1 | | 1/2008 | Chirieleison |
| 2008/0106633 | A1 | * | 5/2008 | Blum ..................... G02C 7/08 348/345 |
| 2009/0066915 | A1 | | 3/2009 | Lai |
| 2009/0189974 | A1 | | 7/2009 | Deering |
| 2009/0279046 | A1 | | 11/2009 | Dreher et al. |
| 2009/0303212 | A1 | | 12/2009 | Akutsu et al. |
| 2010/0053539 | A1 | | 3/2010 | Lin |
| 2011/0018903 | A1 | | 1/2011 | Lapstun et al. |
| 2011/0019258 | A1 | * | 1/2011 | Levola ................. G02B 6/0035 359/238 |
| 2011/0051087 | A1 | | 3/2011 | Inoue et al. |
| 2011/0199202 | A1 | | 8/2011 | De Mers et al. |
| 2011/0213462 | A1 | | 9/2011 | Holladay |
| 2011/0242277 | A1 | * | 10/2011 | Do ......................... H04N 5/272 348/43 |
| 2011/0279277 | A1 | * | 11/2011 | Li-Chung ............ G06Q 10/109 340/573.7 |
| 2012/0007959 | A1 | | 1/2012 | Kwon et al. |
| 2012/0013389 | A1 | | 1/2012 | Thomas et al. |
| 2012/0038549 | A1 | | 2/2012 | Mandella et al. |
| 2012/0092618 | A1 | | 4/2012 | Yoo et al. |
| 2012/0113235 | A1 | | 5/2012 | Shintani |
| 2012/0127062 | A1 | | 5/2012 | Bar-Zeev et al. |
| 2012/0127422 | A1 | | 5/2012 | Tian et al. |
| 2012/0133891 | A1 | | 5/2012 | Jiang |
| 2012/0140044 | A1 | | 6/2012 | Galstian et al. |
| 2012/0154277 | A1 | | 6/2012 | Bar-Zeev et al. |
| 2012/0169730 | A1 | | 7/2012 | Inoue |
| 2012/0206485 | A1 | | 8/2012 | Osterhout et al. |
| 2012/0212499 | A1 | | 8/2012 | Haddick et al. |
| 2012/0212508 | A1 | | 8/2012 | Kimball |
| 2012/0242698 | A1 | | 9/2012 | Haddick et al. |
| 2012/0290401 | A1 | | 11/2012 | Neven |
| 2012/0293773 | A1 | | 11/2012 | Publicover et al. |
| 2012/0307208 | A1 | | 12/2012 | Trousdale |
| 2013/0044042 | A1 | | 2/2013 | Olsson et al. |
| 2013/0050432 | A1 | | 2/2013 | Perez et al. |
| 2013/0050646 | A1 | | 2/2013 | Nanbara |
| 2013/0072828 | A1 | | 3/2013 | Sweis et al. |
| 2013/0093997 | A1 | * | 4/2013 | Utsunomiya .......... A61B 3/102 351/206 |
| 2013/0107066 | A1 | * | 5/2013 | Venkatraman ..... H04N 5/23248 348/208.4 |
| 2013/0127980 | A1 | | 5/2013 | Haddick et al. |
| 2013/0135203 | A1 | | 5/2013 | Croughwell, III |
| 2013/0147836 | A1 | | 6/2013 | Small et al. |
| 2013/0194323 | A1 | | 8/2013 | Choi et al. |
| 2013/0215504 | A1 | | 8/2013 | Kim et al. |
| 2013/0241805 | A1 | | 9/2013 | Gomez |
| 2013/0241927 | A1 | | 9/2013 | Vardi |
| 2013/0278631 | A1 | | 10/2013 | Border et al. |
| 2013/0335301 | A1 | | 12/2013 | Wong et al. |
| 2013/0335404 | A1 | | 12/2013 | Westerinen et al. |
| 2013/0335833 | A1 | | 12/2013 | Liao et al. |
| 2013/0342572 | A1 | | 12/2013 | Poulos et al. |
| 2014/0078175 | A1 | | 3/2014 | Forutanpour et al. |
| 2014/0160157 | A1 | | 6/2014 | Poulos et al. |
| 2014/0225915 | A1 | | 8/2014 | Theimer et al. |
| 2014/0225918 | A1 | | 8/2014 | Mittal et al. |
| 2014/0232746 | A1 | | 8/2014 | Ro et al. |
| 2014/0240351 | A1 | | 8/2014 | Scavezze et al. |
| 2014/0267400 | A1 | | 9/2014 | Mabbutt et al. |
| 2014/0267420 | A1 | | 9/2014 | Schowengerdt et al. |
| 2014/0282224 | A1 | | 9/2014 | Pedley |
| 2014/0327875 | A1 | | 11/2014 | Blum et al. |
| 2014/0354514 | A1 | | 12/2014 | Aronsson |
| 2014/0375680 | A1 | | 12/2014 | Ackerman et al. |
| 2015/0002542 | A1 | | 1/2015 | Chan et al. |
| 2015/0035861 | A1 | | 2/2015 | Salter et al. |
| 2015/0234184 | A1 | | 8/2015 | Schowengerdt et al. |
| 2015/0235427 | A1 | | 8/2015 | Nobori et al. |
| 2015/0235632 | A1 | | 8/2015 | Liu et al. |

(56) References Cited

U.S. PATENT DOCUMENTS

| | | |
|---|---|---|
| 2015/0070391 A1 | 9/2015 | Nishimaki et al. |
| 2016/0034032 A1 | 2/2016 | Jeong |
| 2016/0035139 A1 | 2/2016 | Fuchs et al. |
| 2016/0062454 A1 | 3/2016 | Wang et al. |
| 2016/0171772 A1 | 6/2016 | Ryznar et al. |
| 2016/0189432 A1 | 6/2016 | Bar-Zeev et al. |
| 2016/0196603 A1 | 7/2016 | Perez et al. |
| 2016/0299360 A1 | 10/2016 | Fonte et al. |
| 2016/0370605 A1 | 12/2016 | Ain-Kedem |
| 2017/0092235 A1 | 3/2017 | Osman et al. |

FOREIGN PATENT DOCUMENTS

| | | |
|---|---|---|
| CN | 1141602 | 3/2004 |
| CN | 1527126 | 9/2004 |
| CN | 1604014 | 4/2005 |
| CN | 1645244 | 7/2005 |
| CN | 1653374 A | 8/2005 |
| CN | 1901833 | 1/2007 |
| CN | 1912672 | 2/2007 |
| CN | 2868183 Y | 2/2007 |
| CN | 1951314 | 4/2007 |
| CN | 101069106 | 11/2007 |
| CN | 101072534 | 11/2007 |
| CN | 101097293 A | 1/2008 |
| CN | 101103902 | 1/2008 |
| CN | 201005945 | 1/2008 |
| CN | 101116609 | 2/2008 |
| CN | 101155258 | 4/2008 |
| CN | 101194198 | 6/2008 |
| CN | 101430429 | 5/2009 |
| CN | 201360319 | 9/2009 |
| CN | 201352278 Y | 11/2009 |
| CN | 101900927 | 1/2010 |
| CN | 101662696 | 3/2010 |
| CN | 201464738 | 5/2010 |
| CN | 101782685 | 7/2010 |
| CN | 101819331 A | 9/2010 |
| CN | 101819334 | 9/2010 |
| CN | 201637953 | 11/2010 |
| CN | 101917638 | 12/2010 |
| CN | 201754203 | 3/2011 |
| CN | 102008288 | 4/2011 |
| CN | 102083390 | 6/2011 |
| CN | 102203850 | 9/2011 |
| CN | 102292017 | 12/2011 |
| CN | 102419631 | 4/2012 |
| CN | 102481097 | 5/2012 |
| CN | 101149254 | 6/2012 |
| CN | 102487393 | 6/2012 |
| CN | 202267785 | 6/2012 |
| CN | 102572483 | 7/2012 |
| CN | 102576154 | 7/2012 |
| CN | 202383380 U | 8/2012 |
| CN | 102918444 | 2/2013 |
| CN | 102939557 A | 2/2013 |
| CN | 102981270 | 3/2013 |
| CN | 103054695 | 4/2013 |
| CN | 103065605 | 4/2013 |
| CN | 103150013 | 6/2013 |
| CN | 103190883 | 7/2013 |
| CN | 103197757 | 7/2013 |
| CN | 103280175 | 9/2013 |
| CN | 103297735 | 9/2013 |
| CN | 103353663 | 10/2013 |
| CN | 103353667 | 10/2013 |
| CN | 103353677 | 10/2013 |
| CN | 103558909 | 2/2014 |
| DE | 19959379 | 7/2000 |
| EP | 2646859 | 10/2013 |
| JP | 03023431 | 1/1991 |
| JP | 2676870 | 11/1997 |
| JP | H09289973 | 11/1997 |
| JP | 3383228 | 3/2003 |
| JP | 2003307466 | 10/2003 |
| JP | 2005058399 | 3/2005 |
| JP | 2007129587 | 5/2007 |
| JP | 201143876 | 3/2011 |
| JP | 2012199621 | 10/2012 |
| JP | 2012247449 | 12/2012 |
| TW | 201012448 A | 4/2010 |
| WO | 2004023167 | 3/2004 |
| WO | 2005077258 | 8/2005 |
| WO | 2012075218 | 6/2012 |
| WO | 2012083415 | 6/2012 |
| WO | 2013074851 | 5/2013 |

OTHER PUBLICATIONS

Jeong, et al. "Tunable microdoublet lens array", Optics Express, vol. 12, Issue 11, May 2004, pp. 2494-2500.

International Search Report dated Apr. 3, 2014 for PCT Application No. PCT/CN2013/088531, 10 pages.

International Search Report dated Feb. 27, 2014 for PCT Application No. PCT/CN2013/088522, 6 pages.

International Search Report dated May 8, 2014 for PCT Application No. PCT/CN2013/088547, 4 pages.

Kim et al., "A 200 s Processing Time Smart Image Sensor for an Eye Tracker using pixel-level analog image processing", IEEE Journal of Solid-State Circuits, vol. 44, No. 9, Sep. 2009, 10 pages.

Hansen et al., "In the eye of the beholder: a survey of models for eyes and gaze", IEEE Transactions on pattern analysis and machine intelligence, vol. 32, No. 3, Mar. 2010, 23 pages.

Office Action dated Feb. 27, 2017 for U.S. Appl. No. 14/783,495, 39 pages.

Office Action dated Apr. 21, 2017 for U.S. Appl. No. 14/781,581, 19 pages.

Office Action dated Apr. 20, 2017 for U.S. Appl. No. 14/781,578, 77 pages.

Office Action dated Mar. 30, 2017 for U.S. Appl. No. 15/028,019, 36 pages.

International Search Report dated May 28, 2014 for PCT Application No. PCT/CN2013/088545, 4 pages.

Office Action dated May 3, 2017 for U.S. Appl. No. 14/781,306, 46 pages.

Office Action dated Jun. 29, 2017 for U.S. Appl. No. 14/783,495, 50 pages.

Office Action dated Jun. 29, 2017 for U.S. Appl. No. 14/783,503, 120 pages.

Gao et al. "Measuring Directionality of the Retinal Reflection with a Shack-Hartmann Wavefront Sensor", Dec. 2009, Optics Express, vol. 17, No. 25, Optical Society of America, 20 pages.

Office Action dated Jul. 12, 2017 for U.S. Appl. No. 14/780,519, 45 pages.

Office Action dated Jun. 8, 2017 for U.S. Appl. No. 14/779,968, 79 pages.

International Search report dated Jun. 12, 2014 for PCT Application No. PCT/CN2013/088554, 4 pages.

International Search Report dated Jan. 8, 2015 for PCT Application No. PCT/CN2014/088242, 2 pages.

International Search Report dated May 5, 2014 for PCT Application No. PCT/CN2013/088544, 4 pages.

International Search Report dated Jun. 5, 2014 for PCT Application No. PCT/CN2013/088549, 4 pages.

Smith, et al., "Determining Driver Visual Attention With One Camera", IEEE Transactions on Intelligent Transportation Systems, vol. 4, No. 4, Dec. 2003, 14 Pages.

Singh, et al., "Human Eye Tracking and Related Issues: A Review", International Journal of Scientific and Research Publications, vol. 2, Issue 9, Sep. 2012, ISSN 2250-3153, 9 pages.

Ji et al., "Real-Time Eye, Gaze and Face Pose Tracking for Monitoring Driver Vigilance", Real-Time Imaging 8, 357-377 (2002) available online at http://www.idealibrary.com, 21 pages.

Office Action dated Dec. 29, 2016 for U.S. Appl. No. 14/780,519, 25 pages.

Office Action dated Nov. 9, 2017 for U.S. Appl. No. 14/781,578, 64 pages.

(56) References Cited

OTHER PUBLICATIONS

Office Action dated Nov. 9, 2017 for U.S. Appl. No. 14/780,519, 24 pages.
Office Action dated Dec. 19, 2017 for U.S. Appl. No. 14/783,503, 78 pages.
Lee et al. "A Robust Eye Gaze Tracking Method Based on a Virtual Eyeball Model", Machine Vision and Applications, (2009) 20:319-337, Springer-Verlag, 2008. 19 pages.
Office Action dated Dec. 14, 2017 for U.S. Appl. No. 14/779,321, 82 pages.
Office Action dated Dec. 15, 2017 for U.S. Appl. No. 14/779,968, 67 pages.
Office Action dated Feb. 5, 2018 for U.S. Appl. No. 14/779,321, 38 pages.
Office Action dated Nov. 17, 2017 for U.S. Appl. No. 14/783,495, 32 pages.
Office Action dated Jun. 29, 2018 for U.S. Appl. No. 14/781,578, 67 pages.
Office Action dated Jun. 25, 2018 for U.S. Appl. No. 14/779,321, 43 pages.
Office Action dated Jun. 14, 2018 for U.S. Appl. No. 14/780,519, 29 pages.
Office Action dated Jul. 13, 2018 for U.S. Appl. No. 14/783,495, 36 pages.
Notice of Allowance dated Sep. 11, 2018 for U.S. Appl. No. 14/780,519, 29 pages.
Office Action dated Sep. 20, 2018 for U.S. Appl. No. 14/779,968, 71 pages.
Notice of Allowance dated Nov. 20, 2018 for U.S. Appl. No. 14/779,321, 31 pages.
Office Action dated Dec. 21, 2018 for U.S. Appl. No. 14/783,495, 35 pages.
Office Action dated Feb. 4, 2019 for U.S. Appl. No. 14/781,578, 69 pages.
International Search Report and Written Opinion received for PCT Application Serial No. PCT/CN2013/088553 dated May 28, 2014, 19 pages (Including English Translation).
Beauchemin et al., "The Computation of Optical Flow", ACM Computing Surveys, vol. 27, No. 3, Sep. 1995, pp. 433-467.
Notice of Allowance dated Apr. 17, 2019 for U.S. Appl. No. 14/783,495, 23 pages.
Office Action dated Apr. 25, 2019 for U.S. Appl. No. 14/779,968, 70 pages.

\* cited by examiner

EYESIGHT-PROTECTION IMAGING APPARATUS AND EYESIGHT-PROTECTION IMAGING METHOD

RELATED APPLICATION

This application is a U.S. National Stage filing under 35 U.S.C. § 371 of international patent cooperation treaty (PCT) application No. PCT/CN2013/088545, filed Dec. 4, 2013, and entitled "EYESIGHT-PROTECTION IMAGING APPARATUS AND EYESIGHT-PROTECTION IMAGING METHOD," which claims priority to Chinese Patent Application No. 201310370346.6, filed with the Chinese Patent Office on Aug. 22, 2013 and entitled "VISION PROTECTION IMAGING APPARATUS AND METHOD", which applications are hereby incorporated herein by reference in their respective entireties.

TECHNICAL FIELD

This application relates to the field of imaging technologies, and in particular, to vision protection imaging.

BACKGROUND

A crystalline lens of an eye is shaped like a biconvex lens and is very elastic. When a ciliary muscle contracts, a suspensory ligament relaxes, and the crystalline lens bulges using its own elasticity, to shorten a focal distance and change a diopter; therefore, the eye can clearly view an object at a near distance. When the eye views an object at a far distance, the ciliary muscle relaxes, and the crystalline lens is in a flat state at this time. If the eye views an object at a near distance for a long time, a ciliary body is in a contracted and strained state for a long time and cannot get enough rest. As a result, the eye may feel fatigue, sore, or painful, or a qualitative change that is difficult to recover may even occur in the crystalline lens, causing refractive errors such as nearsightedness. However, during daily usage of eyes, people spend a lot of time viewing objects at a near distance, for example, reading a book, writing, or viewing various screens (such as screens of a television, a computer, a tablet computer, and a mobile phone), and usually forget to or do not have time to frequently look into the distance and protect vision by letting the ciliary muscle relax for a while.

In prior arts, for example, Taiwan Patent Publication No. TW201012448A, various methods for helping people protect vision are recorded. For example, a panel capable of sliding forward and backward is used, so that people continually adjust focal distances of crystalline lenses of eyes when gazing at the panel, thereby achieving the objective of exercising the eyes. For another example, a fatigue degree of eyes is monitored, and when it is found that the eyes are fatigue, an alarm signal is automatically sent, requesting a user to exercise eyes. All these technologies require interruption of an action such as work or study being currently performed by a user to dedicatedly exercise eyes, and require dedicated eye exercise devices. Some of the devices are difficult to carry and have bad user experience. Therefore, an apparatus and a method which can protect vision of eyes without affecting a business being currently dealt with by a user need be found.

SUMMARY

The following presents a simplified summary in order to provide a basic understanding of some example embodiments disclosed herein. This summary is not an extensive overview. It is intended to neither identify key or critical elements nor delineate the scope of the example embodiments disclosed. Its sole purpose is to present some concepts in a simplified form as a prelude to the more detailed description that is presented later.

An example objective of this application is to provide a vision protection imaging apparatus and method, which are used to protect vision of a user without significantly affecting the normal life of the user.

To achieve the foregoing objective, according to a first example embodiment, this application provides a vision protection imaging apparatus, comprising:

an adjustable lens module, configured to image an object viewed by an eye;

an analysis processing module, configured to determine whether time during which a change amount of a distance between a gaze point of the eye and the eye is within a set range exceeds a set threshold, and in response to the time exceeds the set threshold, send adjustment triggering information to a parameter generating module;

the parameter generating module, configured to generate adjustment information of at least one imaging parameter of the adjustable lens module according to the adjustment triggering information; and a lens adjustment module, configured to adjust the at least one imaging parameter of the adjustable lens module according to the adjustment information of the at least one imaging parameter.

According to a second example embodiment, this application further provides a vision protection imaging method, comprising:

determining whether time during which a change amount of a distance between a gaze point of an eye and the eye is within a set range exceeds a set threshold, and in response to the time exceeds the set threshold, generating adjustment triggering information;

generating adjustment information of at least one imaging parameter of an adjustable lens module according to the adjustment triggering information, where the adjustable lens module is configured to image an object viewed by the eye; and adjusting the at least one imaging parameter of the adjustable lens module according to the adjustment information of the imaging parameter.

In the foregoing technical solutions of embodiments of this application, by determining whether time during which a change amount of a distance between a gaze point of an eye and the eye is within a set range exceeds a set threshold, it is learned whether the eye is in a same state for a long time (especially in a tension state for a long time when the eye views an object at a near distance), and when the eye is in a same state for a long time, an imaging parameter of an adjustable lens module, for example, an adjustable glasses lens, between the eye and a viewed object is adjusted, so that an optical system of the eye is adjusted accordingly as well, thereby exercising the eye. In this way, a probability of occurrence or deterioration of a sight problem such as nearsightedness due to improper use of eyes is reduced without affecting work, study, entertainment, or the like being currently performed by a user.

BRIEF DESCRIPTION OF THE DRAWINGS

The disclosure will become more fully understood from the detailed description given herein below for illustration only, and thus are not limitative of the disclosure, and wherein.

DETAILED DESCRIPTION

A method and an apparatus in this application are described in detail as follows with reference to the accompanying drawings and embodiments.

Figure 1:
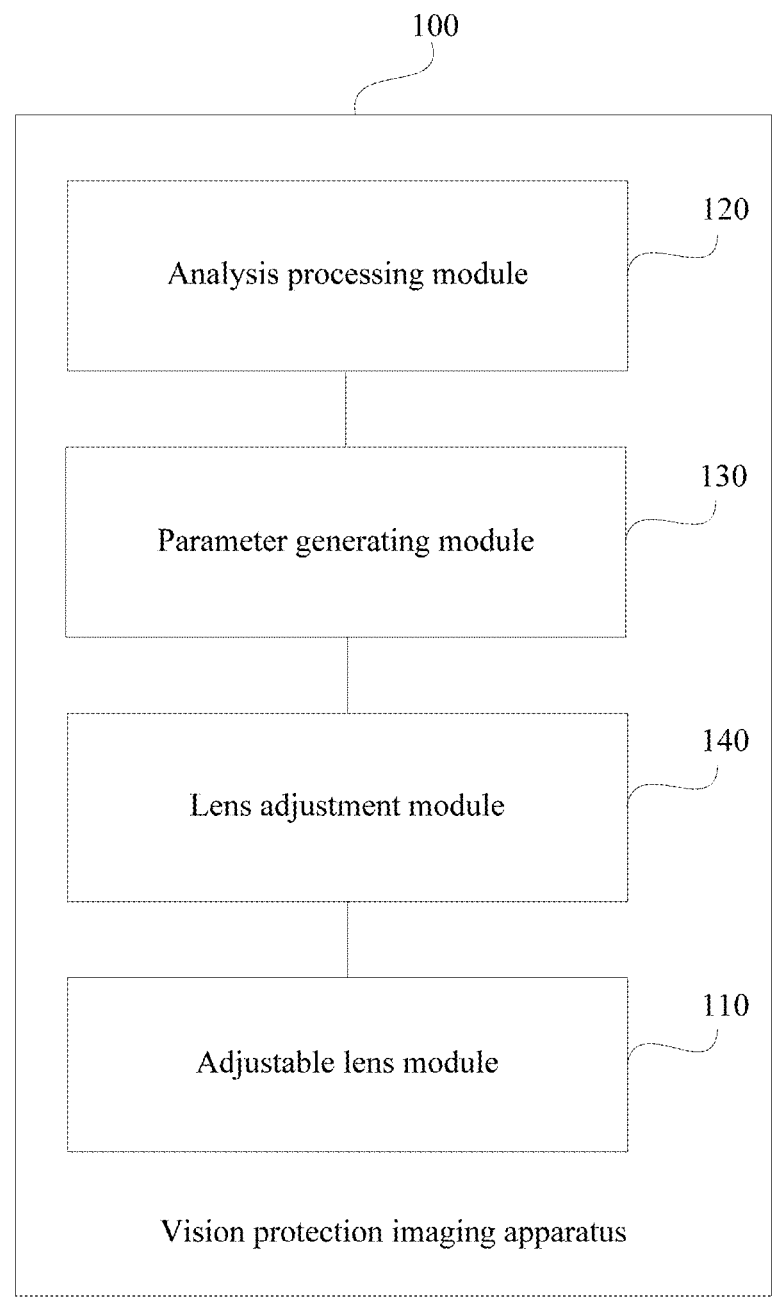
FIG. 1 is a schematic structural block diagram of a vision protection imaging apparatus according to an embodiment of this application.

Some sight problems are caused by improper use of eyes, for example, using eyes to view objects at a near distance for a long time causes refractive errors such as nearsightedness. In order to help a user frequently exercise eye muscles (such as a ciliary muscle and a rectus) so as to prevent eyes from being in a strained adjustment state for a long time, as shown in FIG. 1, an embodiment of this application provides a vision protection imaging apparatus 100, comprising:

an adjustable lens module 110, of which an imaging parameter is adjustable, configured to image an object viewed by an eye;

an analysis processing module 120, configured to determine whether time during which a change amount of a distance between a gaze point of the eye and the eye is within a set range exceeds a set threshold, and when the time exceeds the set threshold, send adjustment triggering information to a parameter generating module 130;

the parameter generating module 130, configured to generate adjustment information of an imaging parameter of the adjustable lens module 110 according to the adjustment triggering information; and a lens adjustment module 140, configured to adjust the imaging parameter of the adjustable lens module 110 according to the adjustment information of the imaging parameter.

In this embodiment, a manner in which the analysis processing module 120 determines whether the time during which the change amount of the distance between the gaze point of the eye and the eye is within the set range exceeds the set threshold, and when the time exceeds the set threshold, sends the adjustment triggering information to the parameter generating module 130 may be:

comparing a distance between a current gaze point of the eye and the eye with a distance between a previous gaze point of the eye and the eye within counted time (that is, from time when counting of time begins to a current moment), so as to determine whether an amount of a change from the distance between the current gaze point of the eye and the eye to a distance between a gaze point of the eye and the eye at any previous moment exceeds a set range;

if the change amount exceeds the set range, re-counting time;

otherwise, continuing counting time, and determining whether counted time exceeds the set threshold; and if the counted time exceeds the set threshold, sending the adjustment triggering information to the parameter generating module 130, and after the adjustment is completed, re-counting time;

otherwise, continuing to determine whether a change amount of a distance between a gaze point of the eye and the eye at a next moment exceeds the set range.

In the embodiment of this application, an image of an object is formed on a retina through the adjustable lens module 110 and an optical system (comprising a crystalline lens) of an eye. In this application, the analysis processing module 120 determines whether time during which a change amount of a distance between a gaze point of an eye and the eye is within a set range exceeds a set threshold, so as to learn whether the eye is in a same state for a long time (especially a tension state for a long time when the eye views an object at a near distance), and when the eye is in a same state for a long time, an imaging parameter of the adjustable lens module 110 is adjusted; in order to keep the image of the object obtained on the retina unchanged or basically unchanged, a brain controls the optical system of the eye to be adjusted accordingly as well, thereby exercising the eye. In this way, a probability of occurrence or deterioration of a sight problem such as nearsightedness due to improper use of eyes is reduced without affecting work, study, entertainment, or the like being currently performed by a user.

In a possible implementation manner of the embodiment of this application, the vision protection imaging apparatus 100 may be an apparatus that is easy to carry and convenient to use, for example, glasses (comprising frame glasses, contact lenses, goggles, or the like), and the adjustable lens module 110 is a lens of the glasses. Especially for a user who has a sight problem such as a refractive error and therefore needs to wear refractive correction glasses, the apparatus in this application can be directly implemented on the refractive correction glasses, so as to reduce a probability that the sight problem of the user further deteriorates or reduce a deterioration degree of the sight problem of the user while correcting vision of the user or even mitigate the sight problem such as the refractive error of the user. In this case, the user does not need an additional device to protect an eye, and therefore no extra burden is brought to the work, life, or the like of the user.

Certainly, in other possible implementation manners of the embodiment of this application, the vision protection imaging apparatus may also be, for example, another optical device used in cooperation with eyes of a user, such as a helmet eye shield, a front windshield of a cab, or a microscope.

The adjustable lens module 110 in the embodiment of this application changes a light propagation manner by changing a structure or a position of the adjustable lens module 110. The adjustable lens module 110 may be formed by a single lens whose imaging parameter is adjustable, or may be formed by a lens group comprising multiple lenses, or may be an optical system comprising a lens and other optical devices.

Preferably, in some possible implementation manners of the embodiment of this application, the adjustable lens module 110 may comprise an electronic adjustable lens, such as a liquid or liquid crystal lens disclosed in U.S. Patent Publication No. US20070211207A1 and U.S. Pat. No. 4,572,616A. By controlling a liquid or a liquid crystal in the lens, an imaging parameter such as a shape or a refractive index of the lens is changed quickly. In a case in which the apparatus in this application is applied to a portable and wearable device such as glasses, using a single electronic adjustable lens as the adjustable lens module 110 can make the apparatus smaller, lighter, and more convenient to carry, and the manner in which the electronic adjustable lens is applied to glasses already has business applications, for example, electronic focusing glasses Empower launched by the Pixeloptics company.

Besides the foregoing electronic adjustable lens, a lens group comprising multiple lenses may also be used to form the adjustable lens module 110. For example, the parameter of the adjustable lens module 110 is adjusted by changing positions of the multiple lenses and optical axis angles of the lenses and by eccentrically arranging the optical axis of the multiple lenses, where a part or all of the multiple lenses are adjustable lenses.

In a possible implementation manner of the embodiment of this application, preferably, the adjustable imaging parameter of the adjustable lens module 110 is mainly an imaging parameter related to exercising of eyes, for example, a focal distance of the adjustable lens module 110. When the focal distance of the adjustable lens module 110 is changed, in order to ensure that a clear image of the object is formed on the retina, a focal distance of the optical system of the eye also necessarily needs to be changed accordingly; for example, a ciliary muscle moves to cause a change of a shape of the crystalline lens, thereby exercising the eye and protecting vision.

Besides the focal distance of the adjustable lens module 110, in a possible implementation manner of the embodiment of this application, preferably, the adjustable imaging parameter of the adjustable lens module 110 may also comprise an optical axis direction of the adjustable lens module 110. By adjusting the optical axis direction of the adjustable lens module 110, eye muscles related to rolling of an eyeball, such as an eye rectus and an eye oblique muscle, can be exercised, thereby achieving the objective of vision protection.

Only the focal distance or the optical axis direction of the adjustable lens module 110 is adjustable, or both the focal distance and the optical axis direction are adjustable. Besides, in other possible implementation manners of the embodiment of this application, besides the focal distance and the optical axis direction, in order to better exercise the eye and/or in order to form a better image of the object based on adjustment of other parameters, other imaging parameters of the adjustable lens module 110 may also be adjustable, and are not listed one by one herein.

Figure 2A:
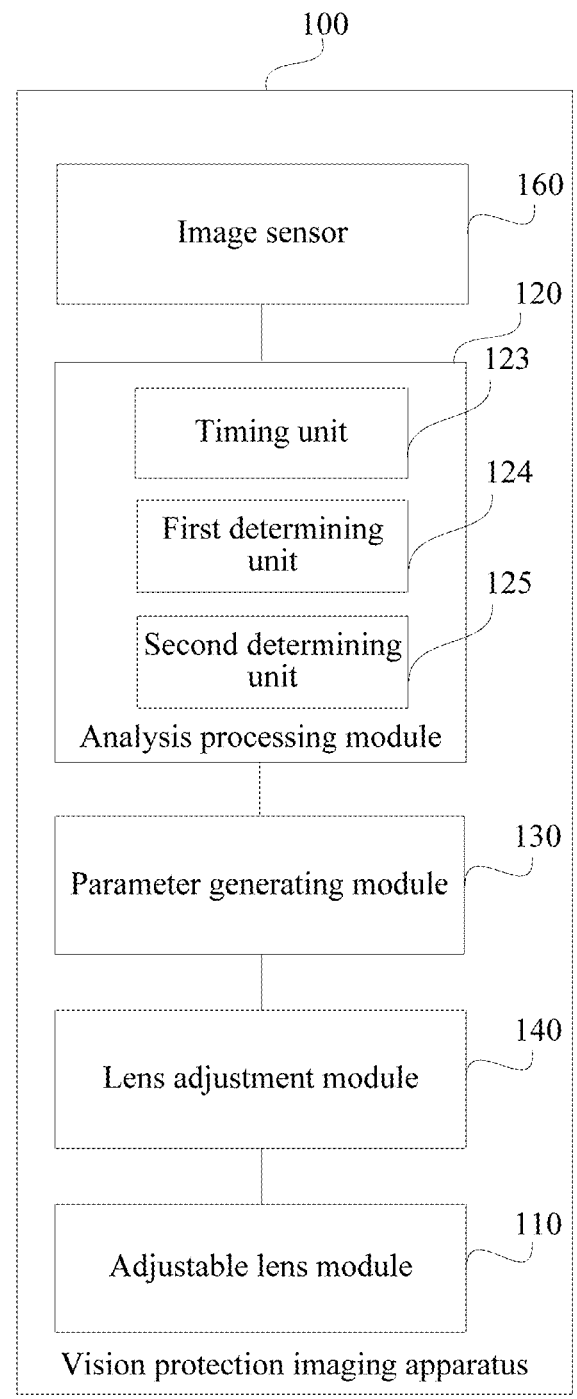
FIG. 2a to FIG. 2d are schematic structural block diagrams of several other vision protection imaging apparatuses according to an embodiment of this application.

As shown in FIG. 2a, in a possible implementation manner of the embodiment of this application, the analysis processing module 120 comprises:

a timing unit 123, configured to perform the foregoing time counting function, and when the change amount of the distance between the gaze point of the eye and the eye exceeds the set range or after adjustment of the imaging parameter of the adjustable lens module is completed, re-count time. The time counting function of the timing unit 123 may be implemented by a program, or may be implemented by a hardware timer.

In the embodiment of this application, there are multiple methods for determining whether the change amount of the distance between the gaze point of the eye and the eye is within the set range by the analysis processing module 120. For example, by determining a change of an image of a scene viewed by the eye, a change of a depth of a scene viewed by the eye, a change of a posture of the head of a user, or a change of a position of a gaze point of the eye of a user, a conclusion about whether the change amount of the distance between the gaze point of the eye and the eye is within the set range can be drawn. The methods are specifically as follows:

(1) In general, when a user stares at a relatively static object, a change amount of an image obtained by an eye by viewing is small. Therefore, in a possible implementation manner of the embodiment of this application, whether the change amount of the distance between the gaze point of the eye and the eye is within the set range may be determined by determining a change of an image obtained by the eye by viewing. In this implementation manner, the apparatus further comprises:

an image sensor 160, configured to collect an image of a scene viewed by the eye. The image sensor 160 may be a micro camera or the like.

Preferably, in this implementation manner, the analysis processing module 120 comprises:

a first determining unit 124, configured to determine whether time during which a change amount of the image is within a set range exceeds the set threshold.

In this implementation manner, the first determining unit 124 compares a currently collected image with an image previously collected within counted time, so as to determine whether an amount of a change from the current image to any previously collected image exceeds a set range; and if the change amount does not exceed the set range, counting of time is continued, and the first determining unit 124 determines whether the counted time exceeds the set threshold; otherwise, time is re-counted. When it is determined that the counted time exceeds the set threshold, the analysis processing module sends the adjustment triggering information to the parameter generating module 130.

In a possible implementation manner of the embodiment of this application, methods such as an optical flow algorithm (S. S. Beauchemin, J. L. Barron (1995). The computation of optical flow. ACM New York, USA) may be used to detect a change degree of the image.

A user may read content which constantly changes and is displayed on a display apparatus or a book or may even read or view a book, a mobile phone, a tablet computer, or the like while moving. Therefore, in this process, a change amount of an image collected by the image sensor may be great, but there is basically no big change in a distance between a gaze point of an eye of the user and the eye. After the set time threshold is exceeded, the eye needs to be exercised. Therefore, in a possible implementation manner of the embodiment of this application, the analysis processing module comprises:

a second determining unit 125, configured to determine, according to the image, whether the scene comprises an object having a presetted feature, and when the scene comprises an object having a presetted feature, determine whether time during which the scene comprises the object having the presetted feature exceeds the set threshold.

For example, when a user takes a vehicle for travel, the user reads content displayed on a mobile phone. In this case, because the vehicle is moving or other passengers are getting on and off or walking around, the image sensor not only collects the content displayed on the mobile phone, but may also collect backgrounds that change constantly. Besides, the content displayed on the mobile phone also changes frequently. Therefore, determining needs to be performed according to the image collected by the image sensor. For example, if a collected scene comprises a display screen of a mobile phone (or comprises a display screen of a same mobile phone all the time), it is determined that the user is reading content displayed on a mobile phone. Therefore, a change of a distance between an object and a gaze point of an eye of the user is not determined anymore; instead, after time during which the user reads the display screen of the mobile phone reaches a set time threshold, adjustment triggering information is automatically generated.

In this implementation manner, the object having the presetted feature is mainly an object that needs to be viewed at a near distance for a long time, such as a display screen of a display device (a computer, a tablet computer, or a mobile phone) at a near distance, a book, or a newspaper. These objects generally all have a specific technical feature. In a possible implementation manner of the embodiment of this application, the feature comprises one or more of features such as a shape (which is mainly a 2D shape of an object), a material, a texture, and brightness of an object. For example, according to features of an object near a center of the image that a shape of the object is a rectangle and a material of the object is paper, it is determined that the user is reading a book; and according to features that a shape of the object is a rectangle and brightness of the object is brightness specific to a display screen, it is determined that the user is viewing a display device.

Figure 2B:
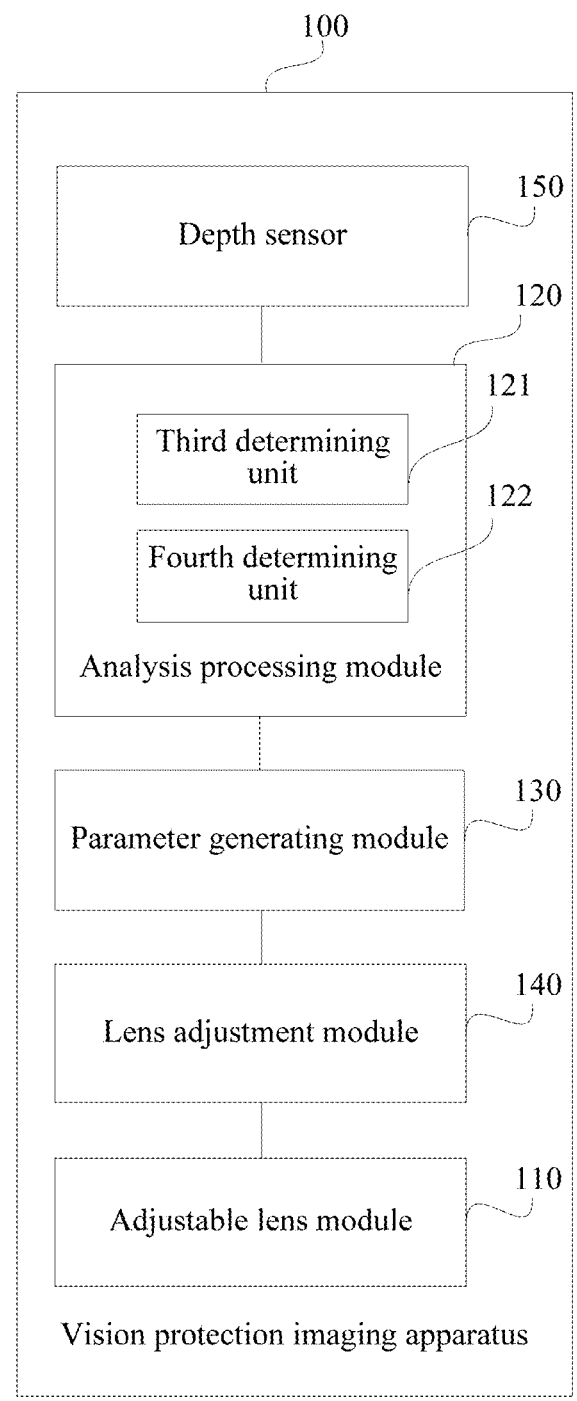
Figure 3:
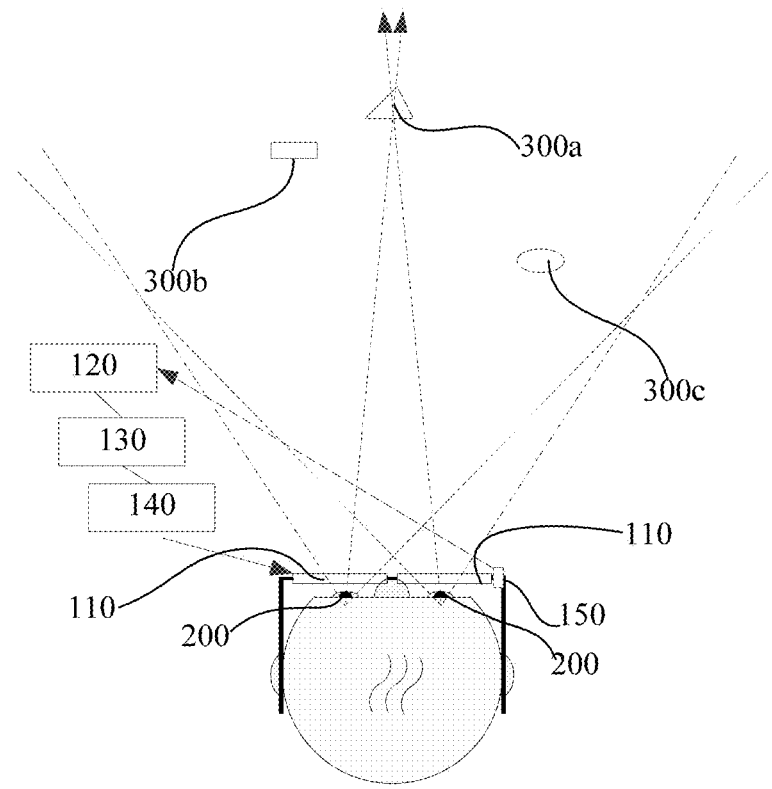
FIG. 3 is a schematic diagram of an application of a vision protection imaging apparatus according to an embodiment of this application.

(2) Similar to the method (1) in which whether the change amount of the distance between the gaze point of the eye and the eye is within the set range is determined by determining a change of an image obtained by the eye by viewing, whether the change amount of the distance between the gaze point of the eye and the eye is within the set range may also be determined by determining a change of depth information of a scene viewed by an eye. As shown in FIG. 2b and FIG. 3, in another possible implementation manner of the embodiment of this application, the apparatus 100 further comprises:

a depth sensor 150, configured to collect depth information of a scene viewed by the eye 200.

Figure 4:
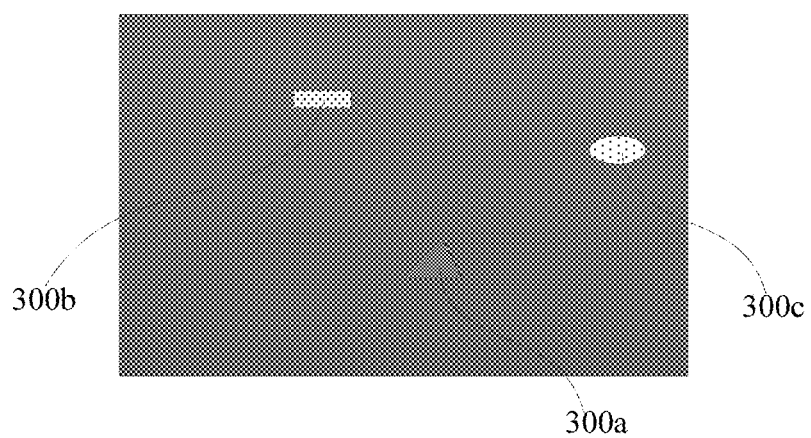
FIG. 4 is a depth diagram obtained by a vision protection imaging apparatus according to an embodiment of this application.

In this implementation manner, the depth information may be, for example, a depth diagram shown in FIG. 4. The scene viewed by the eye 200 comprises three objects 300a, 300a, and 300c, and depths of the objects from the eye 200 are different from each other. When a position of the eye relative to any one of these objects (which is mainly a position in a depth direction) is changed, a position of the object in the depth diagram and/or a color of the object (in the depth diagram, different depths are indicated by different colors) is also changed accordingly. In FIG. 2b, the depth sensor 150 may be disposed on a frame of glasses.

Preferably, in this implementation manner, the analysis processing module 120 comprises:

a third determining unit 121, configured to determine whether time during which a change amount of the depth information is within a set range exceeds the set threshold.

In this implementation manner, the third determining unit 121 compares currently collected depth information such as a depth diagram with depth information previously collected within counted time, so as to determine whether an amount of a change from the current depth information of a scene to any previously collected depth information of the scene exceeds a set range; and if the change amount does not exceed the set range, counting of time is continued, and the third determining unit 121 determines whether the counted time exceeds the set threshold; otherwise, time is re-counted. When it is determined that the counted time exceeds the set threshold, the analysis processing module sends the adjustment triggering information to the parameter generating module 130.

Similar to the foregoing manner in which determining is performed according to an image of a scene viewed by the eye, a case in which a user is viewing a book, a display device, or the like may also occur when depth information of a scene viewed by the eye is used. Therefore, in a possible implementation manner of the embodiment of this application, the analysis processing module 120 comprises:

a fourth determining unit 122, configured to determine, according to the depth information of the scene, whether the scene comprises an object having a presetted feature, and when the scene comprises an object having a presetted feature, determine whether time during which the scene comprises the object having the presetted feature exceeds the set threshold.

Preferably, in this implementation manner, the feature comprises a shape of the object. The shape of the object is mainly a 3D shape of the object. The 3D shape of the object, such as a frame of the object and a concave and convex surface of the object, may be obtained according to the depth information of the object. The object such as a mobile phone, a computer, or another display device, or a book or a newspaper may be determined according to the 3D shape of the object.

Figure 2C:
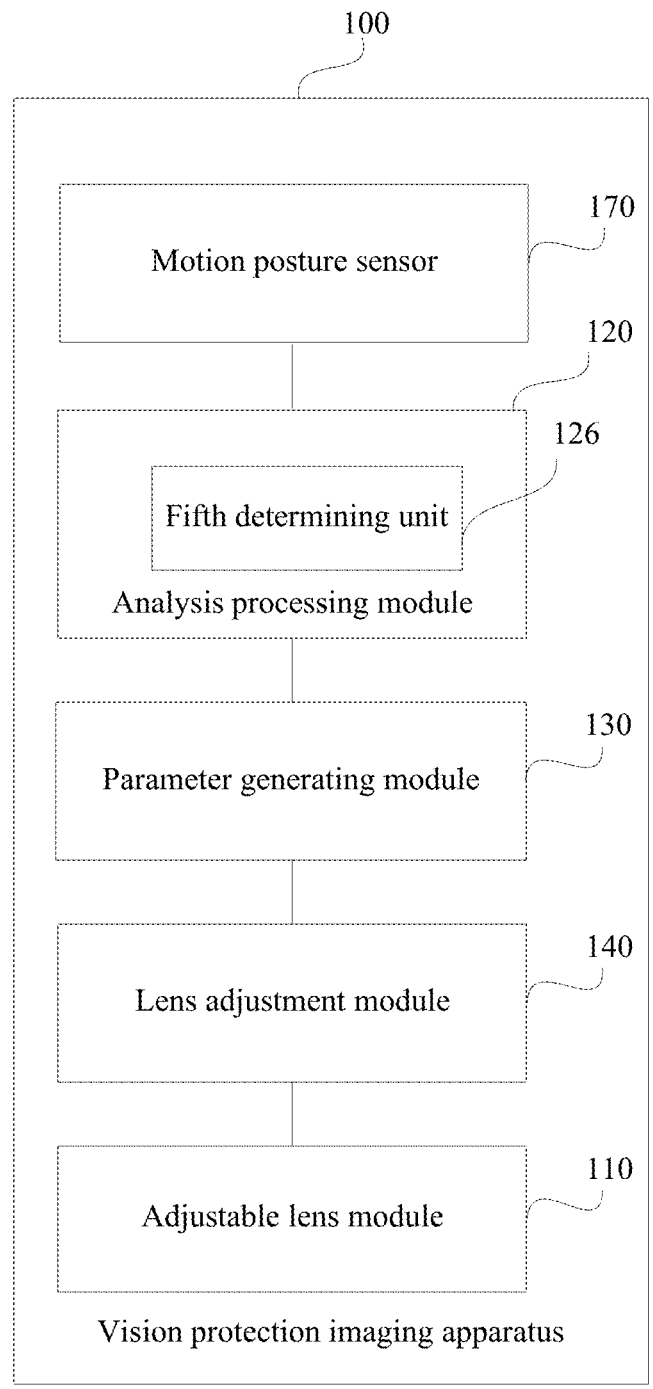

(3) Generally speaking, when a user is viewing a relatively static object or an object within a distance range, a change of a posture of the head is small. Therefore, in a possible implementation manner of the embodiment of this application, whether the change amount of the distance between the gaze point of the eye and the eye is within the set range may be determined by determining a change of a posture of the head of a user. As shown in FIG. 2c, in this implementation manner, the apparatus further comprises:

a motion posture sensor 170, configured to collect posture information of the head of a user.

Preferably, in a possible implementation manner of the embodiment of this application, the analysis processing module 120 comprises:

a fifth determining unit 126, configured to determine, according to the posture information, whether time during which a change amount of a posture of the head of the user is within a set range exceeds the set threshold.

In this implementation manner, the fifth determining unit compares current posture information of the head of the user with posture information of the head of the user previously collected within counted time, so as to determine whether an amount of a change from the current posture information of the head of the user to any previously collected posture information of the head of the user exceeds a set range; and if the change amount does not exceed the set range, counting of time is continued, and the fifth determining unit determines whether the counted time exceeds the set threshold; otherwise, time is re-counted. When it is determined that the counted time exceeds the set threshold, the analysis processing module 120 sends the adjustment triggering information to the parameter generating module 130.

Figure 2D:
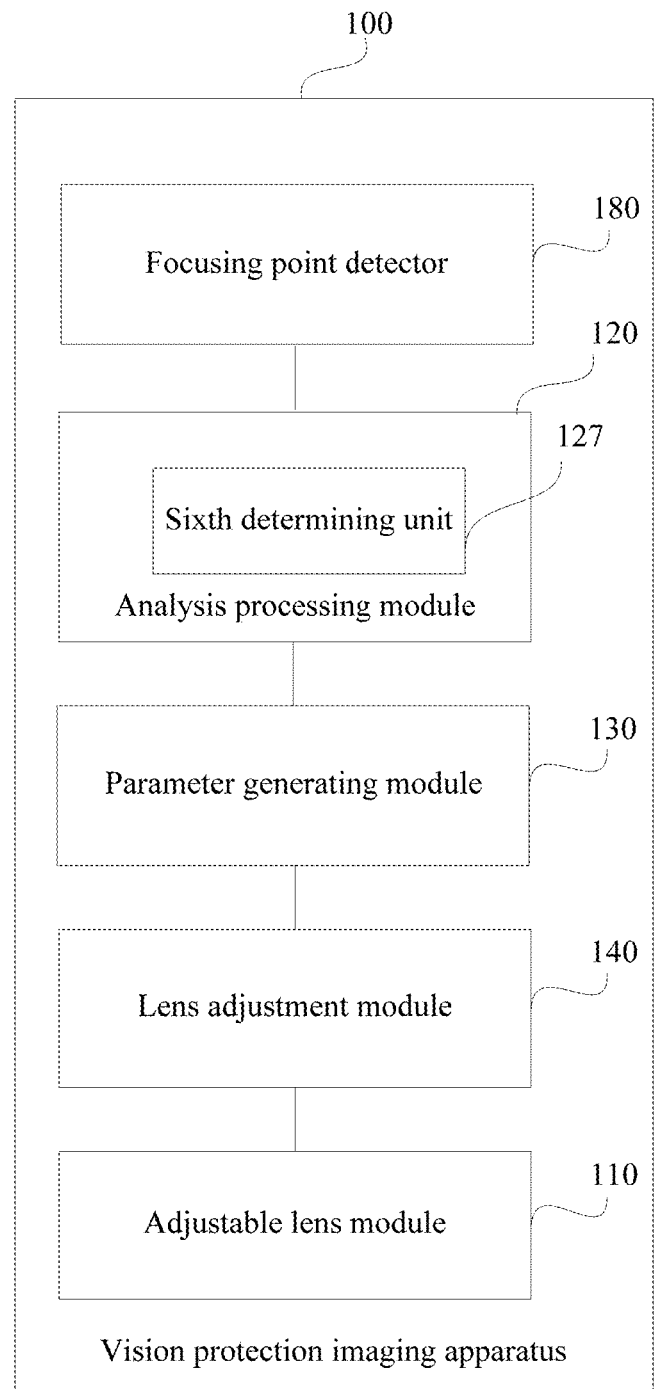

Besides the foregoing several manners, in a possible implementation manner of the embodiment of this application, whether the change amount of the distance between the gaze point of the eye and the eye is within the set range may also be determined by detecting a change of a position of a focusing point of a sight line of the eye. As shown in FIG. 2d, in this implementation manner, the apparatus further comprises:

a focusing point detector 180, configured to obtain a position of a focusing point of a sight line of the eye.

Preferably, in a possible implementation manner of the embodiment of this application, the analysis processing module 120 comprises:

a sixth determining unit 127, configured to determine whether time during which a change amount of the position of the focusing point is within a set range exceeds the set threshold.

Compared with the foregoing several methods, generally speaking, this implementation manner has better determining accuracy because no matter which object the user is viewing, as long as a position of a focusing point of the eye is basically unchanged, the eye needs to be exercised when the set time threshold is exceeded. Certainly, in some possible implementation manners of the embodiment of this application, in order to improve determining accuracy, the analysis processing module may comprise the foregoing multiple determining units and corresponding sensors.

There may be multiple types of focusing point detectors 180, and examples are as follows:

(a) A pupil direction detector is configured to detect an optical axis direction of an eye, and then a depth sensor (for example, infrared distance meter) is configured to obtain a depth of a scene which the eye gazes at, thereby obtaining a position of a focusing point of a sight line of the eye. This technology is a prior art and is therefore not described in detail in this implementation manner.

(b) Optical axis directions of two eyes are detected separately, and then an intersection of the optical axis directions of the two eyes is obtained, thereby obtaining a position of a focusing point of a sight line of the eye. This technology is also a prior art and is therefore not described in detail in this implementation manner.

(c) According to an optical parameter of a light path between an image collection device and an eye when a clearest image presented on an imaging surface of the eye is collected, a position of a focusing point of a sight line of the eye is obtained. In this implementation manner, the focusing point detector may be one of the following focusing point detectors shown in FIG. 5a to FIG. 5f, FIG. 6, and FIG. 7.

Figure 5A:
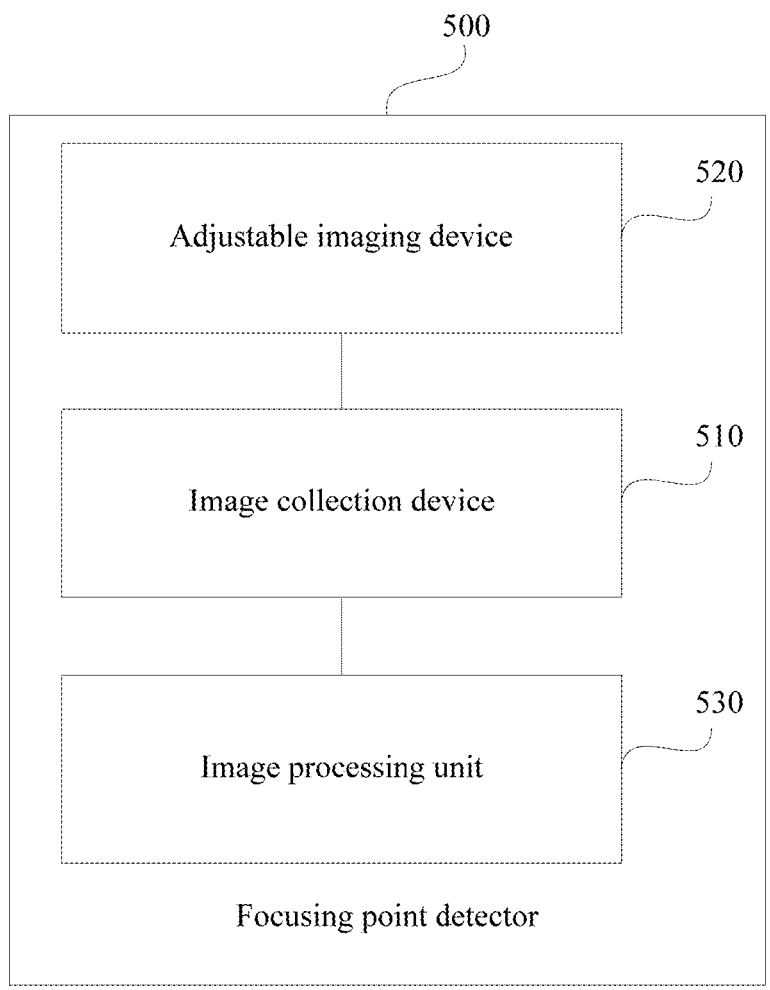
FIG. 5a is a structural block diagram of a focusing point detector of a vision protection imaging apparatus according to an embodiment of this application.

As shown in FIG. 5a, the focusing point detector 500 comprises:

an image collection device 510, configured to collect an image presented on a fundus of the eye;

an adjustable imaging device 520, configured to adjust an imaging parameter of a light path between the eye and the image collection device 510, so that the image collection device 510 obtains a clearest image; and an image processing unit 530, configured to process the image obtained by the image collection device 510, and obtain the position of the focusing point of the eye according to the imaging parameter of the light path between the image collection device 510 and the eye and an optical parameter of the eye when the clearest image is obtained.

The focusing point detector 500 analyzes an image on a fundus of the eye, obtains an optical parameter of the eye when the image collection device obtains a clearest image, and then calculates a current position of a focusing point of the eye, thereby providing a basis for further implementing a self-adaptive operation of the eye.

The image presented on the "fundus" is mainly an image presented on the retina. The image may be an image of the fundus, or may be an image of another object projected onto the fundus. The eye may be an eye of a human, or may be an eye of another animal.

Figure 5B:
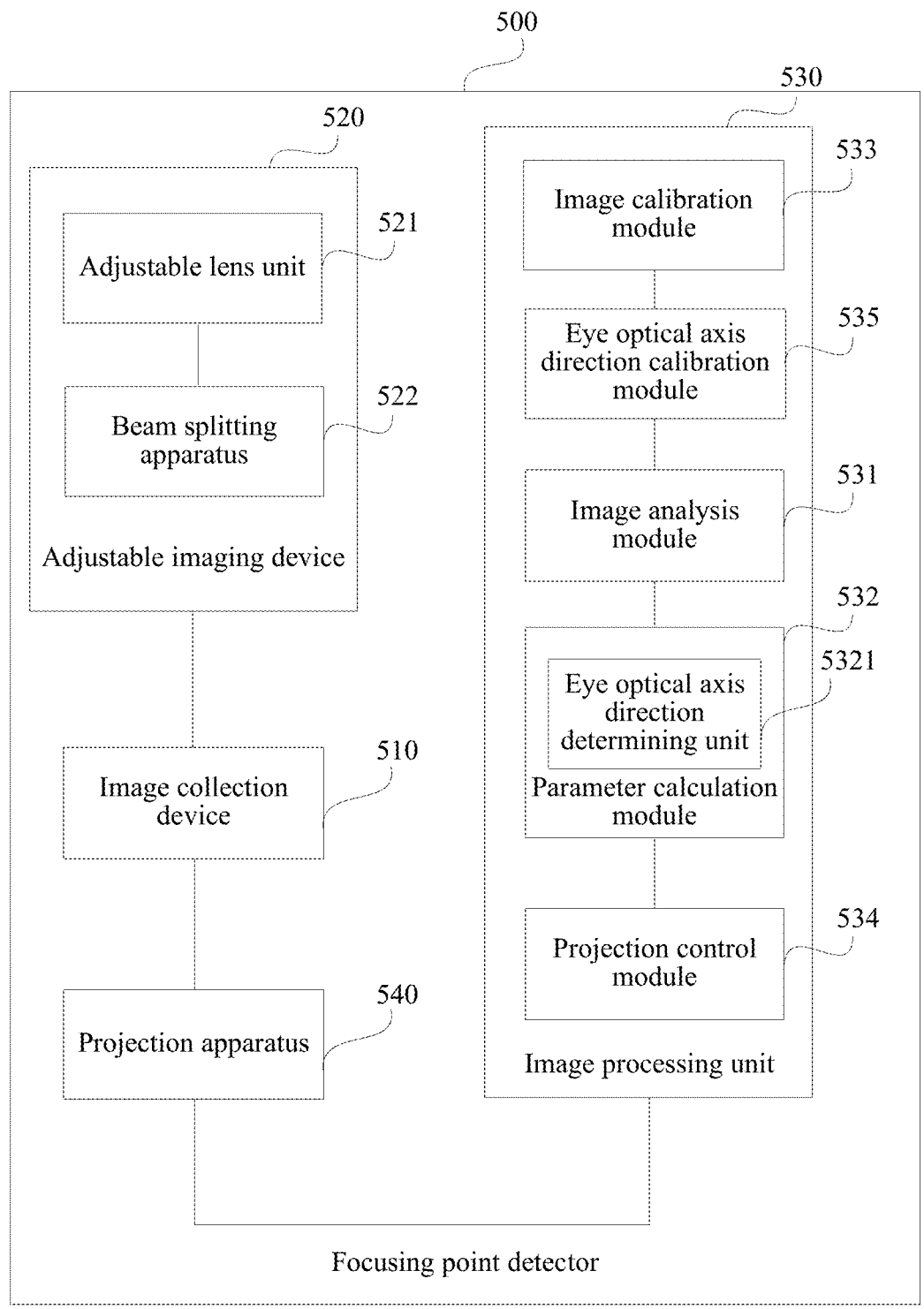
FIG. 5b is a structural block diagram of another focusing point detector of a vision protection imaging apparatus according to an embodiment of this application.

As shown in FIG. 5b, in a possible implementation manner of the embodiment of this application, the image collection device 510 is a micro camera. In another possible implementation manner of the embodiment of this application, a photosensitive imaging device such as a CCD or a CMOS may be directly used as the image collection device 510.

In a possible implementation manner of the embodiment of this application, the adjustable imaging device 520 comprises: an adjustable lens unit 521, located on the light path between the eye and the image collection device 510, a focal distance of the adjustable lens unit being adjustable or a position of the adjustable lens unit on the light path being adjustable. By using the adjustable lens unit 521, an equivalent focal distance of a system between the eye and the image collection device 510 is adjustable. By adjusting the adjustable lens unit 521, the image collection device 510 obtains the clearest image on the fundus when the adjustable lens unit 521 is in a certain position or state. In this implementation manner, the adjustable lens unit 521 is adjusted continuously in real time in the detecting process.

Preferably, in a possible implementation manner of the embodiment of this application, the adjustable lens unit 521 is a focal-distance-adjustable lens, configured to adjust a refractive index and/or a shape of the focal-distance-adjustable lens, so as to adjust a focal distance of the focal-distance-adjustable lens. Specifically, (1) the focal distance is adjusted by adjusting the curvature of at least one surface of the focal-distance-adjustable lens; for example, the curvature of the focal-distance-adjustable lens is adjusted by increasing or reducing a liquid medium in a cavity formed by two transparent layers; (2) the focal distance is adjusted by changing a refractive index of the focal-distance-adjustable lens; for example, the focal-distance-adjustable lens is filled with a specific liquid crystal medium, and by adjusting a voltage of an electrode corresponding to the liquid crystal medium, an arranging manner of the liquid crystal medium is adjusted, thereby changing the refractive index of the focal-distance-adjustable lens.

In another possible implementation manner, the adjustable lens unit 521 comprises: a lens group, configured to adjust relative positions of lenses in the lens group, so as to adjust a focal distance of the lens group.

Besides the foregoing two manners in which a light path parameter of a system is changed by adjusting a feature of the adjustable lens unit 521, the light path parameter of the system may also be changed by adjusting a position of the adjustable lens unit 521 on the light path.

Preferably, in a possible implementation manner of the embodiment of this application, in order not to affect experience of viewing the object by the user and in order that the system can be portable and applied to a wearable device, the adjustable imaging device 520 further comprises: a beam splitting apparatus 522, configured to form light transfer paths between the eye and the viewed object and between the eye and the image collection device 510. In this way, the light path can be folded, the volume of the system can be reduced, and at the same time, other experience of the user is affected as little as possible.

Preferably, in this implementation manner, the beam splitting apparatus comprises: a first beam splitting unit, located between the eye and the viewed object, and configured to transmit light from the viewed object to the eye, and transfer light from the eye to the image collection device.

The first beam splitting unit may be a spectroscope, a beam splitting optical waveguide (comprising an optical fiber), or another suitable beam splitting device.

In a possible implementation manner of the embodiment of this application, the image processing unit 530 of the focusing point detector 500 comprises a light path calibration module, configured to calibrate the light path of the system, for example, align and calibrate an optical axis of the light path, so as to ensure measurement accuracy.

In a possible implementation manner of the embodiment of this application, the image processing unit 530 comprises:

an image analysis module 531, configured to analyze an image obtained by the image collection device, to find a clearest image; and a parameter calculation module 532, configured to calculate, according to the clearest image and a known imaging parameter of the system when the clearest image is obtained, the optical parameter of the eye.

In this implementation manner, by using the adjustable imaging device 520, the image collection device 510 can obtain a clearest image, but the clearest image needs to be found by using the image analysis module 531; in this case, the optical parameter of the eye can be calculated according to the clearest image and the known light path parameter of the system. The optical parameter of the eye may comprise an optical axis direction of the eye.

In a possible implementation manner of the embodiment of this application, preferably, the focusing point detector 500 further comprises: a projection apparatus 540, configured to project a light spot onto the fundus. In a possible implementation manner, a micro projector may be configured to implement the function of the projection apparatus.

The projected light spot may not have a specific pattern and is only used to illuminate the fundus.

Figure 5C:
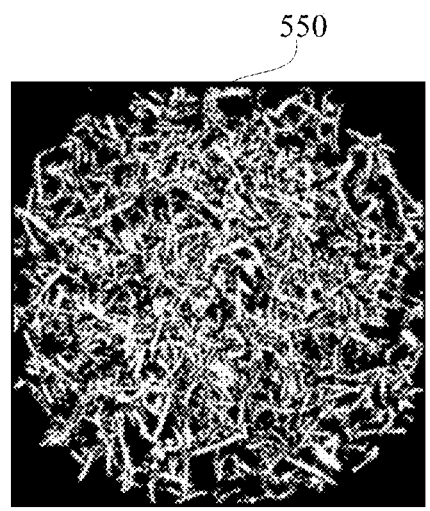
FIG. 5c is a schematic diagram of a light spot pattern used by a focusing point detector of a vision protection imaging apparatus according to an embodiment of this application.
Figure 5D:
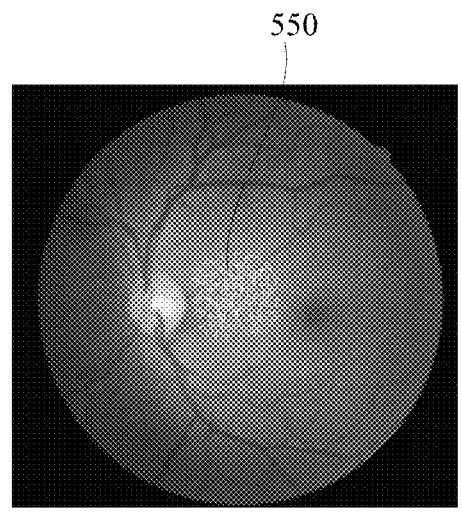
FIG. 5d is a schematic diagram of an image which has a light spot pattern and is taken on a fundus by a focusing point detector of a vision protection imaging apparatus according to an embodiment of this application.

In a preferred implementation manner of the embodiment of this application, the projected light spot comprises a pattern with rich features. The rich features of the pattern facilitate detection and improve detection accuracy. FIG. 5*c* is a diagram of an example of a light spot pattern 550. The pattern may be generated by a light spot pattern generator, for example, ground glass. FIG. 5*d* shows an image which is on a fundus and is taken when the light spot pattern 550 is projected.

In order not to affect normal viewing of the eye, preferably, the light spot is an infrared light spot invisible to the eye.

In this case, in order to reduce interference from other spectrums, a filter for transmitting light invisible to the eye may be disposed on an emergent surface of the projection apparatus; and a filter for transmitting light invisible to the eye is disposed on an incident surface of the image collection device.

Preferably, in a possible implementation manner of the embodiment of this application, the image processing unit 530 further comprises:

a projection control module 534, configured to control, according to a result obtained by the image analysis module, brightness of the light spot projected by the projection apparatus.

For example, the projection control module 534 may perform self-adaptive adjustment of brightness according to a feature of the image obtained by the image collection device 510. The feature of the image comprises a feature contrast, a textural feature, and the like of the image.

A special case of controlling the brightness of the light spot projected by the projection apparatus is turning on or off the projection apparatus. For example, when the user continuously gazes at a point, the projection apparatus may be turned off periodically; when the fundus of the user is bright enough, a light source may be turned off, and only information about the fundus is used to detect the distance between the focusing point of the current sight line of the eye and the eye.

Besides, the projection control module 534 may also control, according to ambient light, the brightness of the light spot projected by the projection apparatus.

Preferably, in a possible implementation manner of the embodiment of this application, the image processing unit 530 further comprises: an image calibration module 533, configured to calibrate an image on the fundus, to obtain at least one reference image corresponding to the image presented on the fundus.

The image analysis module 531 compares the image obtained by the image collection device 530 with the reference image, and calculates the clearest image. The clearest image may be an image that is obtained and has the smallest difference from the reference image. In this implementation manner, a difference between a currently obtained image and the reference image is calculated by using an existing image processing algorithm, for example, by using a classic phase-difference auto-focus algorithm.

Preferably, in a possible implementation manner of the embodiment of this application, the parameter calculation module 532 comprises:

an eye optical axis direction determining unit 5321, configured to obtain, according to a feature of the eye when the clearest image is obtained, an optical axis direction of the eye.

The feature of the eye may be obtained from the clearest image, or may be obtained otherwise. The optical axis direction of the eye indicates a gaze direction of the sight line of the eye.

Preferably, in a possible implementation manner of the embodiment of this application, the eye optical axis direction determining unit 5321 comprises: a first determining subunit, configured to obtain, according to a feature of the fundus when the clearest image is obtained, the optical axis direction of the eye. Compared with an optical axis direction of the eye obtained according to features of the pupil and a surface of the eyeball, the optical axis direction of the eye determined according to the feature of the fundus is more accurate.

When the light spot pattern is projected onto the fundus, a size of the light spot pattern may be greater or smaller than that of a visible area of the fundus.

When the area of the light spot pattern is smaller than or equal to that of the visible area of the fundus, a classic feature point matching algorithm (for example, a scale invariant feature transform (SIFT) algorithm) may be used to detect a position of the light spot pattern on the image relative to the fundus, so as to determine the optical axis direction of the eye.

When the area of the light spot pattern is greater than or equal to that of the visible area of the fundus, the optical axis direction of the eye may be determined according to an obtained position of the light spot pattern on the image relative to the original light spot pattern (which is obtained by the image calibration module), so as to determine a sight line direction of the user.

In another possible implementation manner of the embodiment of this application, the eye optical axis direction determining unit 5321 comprises: a second determining subunit, configured to obtain, according to a feature of the pupil of the eye when the clearest image is obtained, the optical axis direction of the eye. The feature of the pupil of the eye may be obtained from the clearest image, or may be obtained otherwise. Obtaining an optical axis direction of an eye according to a feature of a pupil of the eye is a prior art, and is therefore not described herein in detail.

Preferably, in a possible implementation manner of the embodiment of this application, the image processing unit 530 further comprises: an eye optical axis direction calibration module 535, configured to calibrate the optical axis direction of the eye, so as to more accurately determine the optical axis direction of the eye.

In this implementation manner, the known imaging parameter of the system comprises a fixed imaging parameter and a real-time imaging parameter, where the real-time imaging parameter is parameter information of the adjustable lens unit when the clearest image is obtained, and the parameter information may be obtained by performing real-time recording when the clearest image is obtained.

Figure 5E:
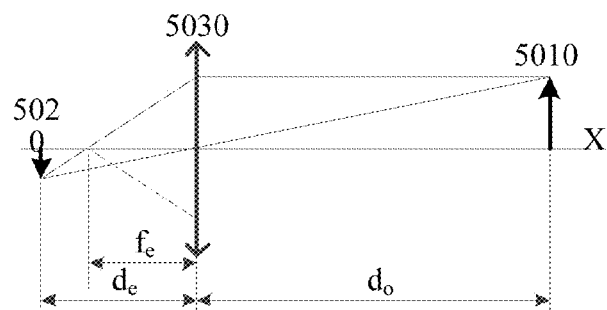
FIG. 5e is a schematic diagram of an eye-imaging light path of a focusing point detector of a vision protection imaging apparatus according to an embodiment of this application.

After the current optical parameter of the eye is obtained, the distance between the focusing point of the eye and the eye may be obtained by calculating, which is specifically as follows:

FIG. 5e is a schematic diagram of imaging by an eye. With reference to a lens imaging formula in a classic optics theory, a formula (1) may be obtained according to FIG. 5e:

$$\frac{1}{d_o} + \frac{1}{d_e} = \frac{1}{f_e}, \quad (1)$$

where $d_o$ and $d_e$ are respectively a distance between an object 5010 currently viewed by an eye and an eye equivalent lens 5030 and a distance between a real image 5020 on a retina and the eye equivalent lens 5030, $f_e$ is an equivalent focal distance of the eye equivalent lens 5030, and X is a sight line direction of an eye (which may be obtained according to an optical axis direction of the eye).

Figure 5F:
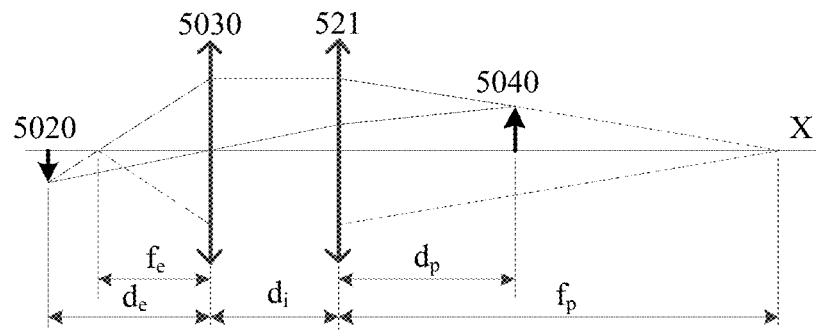
FIG. 5f is a schematic diagram of obtaining, by a focusing point detector, a distance between a focusing point of an eye and the eye according to a known imaging parameter of a system and an optical parameter of the eye, of a vision protection imaging apparatus according to an embodiment of this application.

FIG. 5f is a schematic diagram of obtaining a distance between a focusing point of an eye and the eye according to a known optical parameter of a system and an optical parameter of the eye. In FIG. 5f, a light spot 5040 forms a virtual image (which is not shown in FIG. 5f) through an adjustable lens unit 521. It is assumed that a distance between the virtual image and a lens is x (which is not shown in FIG. 5f), and the following equation set may be obtained with reference to the formula (1):

$$\begin{cases} \dfrac{1}{d_p} - \dfrac{1}{x} = \dfrac{1}{f_p} \\ \dfrac{1}{d_i + x} + \dfrac{1}{d_e} = \dfrac{1}{f_e} \end{cases}, \quad (2)$$

where $d_p$ is an optical equivalent distance between the light spot 5040 and the adjustable lens unit 521, $d_i$ is an optical equivalent distance between the adjustable lens unit 521 and an eye equivalent lens 5030, $f_p$ is a value of a focal distance of the adjustable lens unit 521, and $d_i$ is a distance between the eye equivalent lens 5030 and the adjustable lens unit 521.

It can be learned according to (1) and (2) that the distance $d_o$ between the currently viewed object 5010 (the focusing point of the eye) and the eye equivalent lens 5030 satisfies the following formula (3):

$$d_o = d_i + \frac{d_p \cdot f_p}{f_p - d_p} \quad (3)$$

According to the foregoing distance between the viewed object 5010 and the eye, which is obtained by calculating, and the optical axis direction of the eye, which can be obtained according to a previous record, the position of the focusing point of the eye can be easily obtained, thereby providing a basis for subsequent further eye-related interaction.

Figure 6:
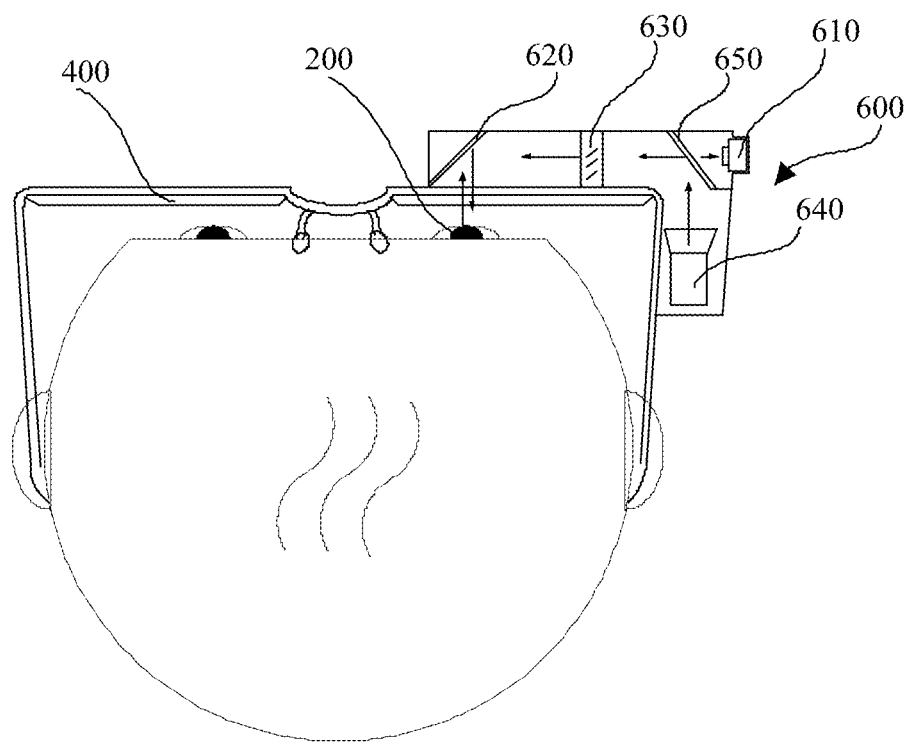
FIG. 6 is a schematic diagram of applying a focusing point detector, to glasses, of a vision protection imaging apparatus according to an embodiment of this application.

FIG. 6 shows an embodiment of a focusing point detector 600 applied to glasses 400 (the glasses 400 may be the imaging apparatus in the embodiment of this application) according to a possible implementation manner of the embodiment of this application. The focusing point detector 600 comprises the content recorded in the implementation manner shown in FIG. 5b. Specifically, as can be seen from FIG. 6, in this implementation manner, the focusing point detector 600 in this implementation manner is integrated on a right side of the glasses 400 (this application is not limited thereto), and comprises:

a micro camera 610, having a same function as that of the image collection device recorded in the implementation manner in FIG. 5b, and disposed on a right outer side of the glasses 400 in order not to affect a sight line of a user for normally viewing an object;

a first spectroscope 620, having a same function as that of the first beam splitting unit recorded in the implementation manner in FIG. 5b, disposed at an inclination angle at an intersection of a gaze direction of an eye 200 and an incident direction of the camera 610, and transmitting light of a viewed object that enters the eye 200 and reflecting light from the eye to the camera 610; and a focal-distance-adjustable lens 630, having a same function as that of the focal-distance-adjustable lens recorded in the implementation manner in FIG. 5b, located between the first spectroscope 620 and the camera 610, and adjusting a value of a focal distance in real time, so that the camera 610 can take a clearest image on a fundus when the focal distance is of a certain value.

In this implementation manner, a image processing unit is not shown in FIG. 6, and a function of the image processing unit is the same as that of the image processing unit shown in FIG. 5b.

In general, brightness on a fundus is insufficient. Therefore, the fundus had better be illuminated. In this implementation manner, a light source 640 is configured to illuminate the fundus. In order not to affect user experience, the light source 640 preferably emits light invisible to the eye, and is preferably a light source emitting near-infrared light which does not affect the eye 200 much and to which the camera 610 is sensitive.

In this implementation manner, the light source 640 is located on an outer side of a frame on the right side of the glasses, and therefore, a second spectroscope 650 needs to be used in combination with the first spectroscope 620, so as to complete transfer of the light emitted by the light source 640 to the fundus. In this implementation manner, the second spectroscope 650 is located in front of an incident surface of the camera 610, and therefore, light from the fundus to the second spectroscope 650 also needs to be transmitted by the second spectroscope 650.

It can be seen that in this implementation manner, in order to improve user experience and improve collection clarity of the camera 610, the first spectroscope 620 may preferably have features of high infrared reflectivity and high visible light transmissivity. For example, an infrared reflective film may be disposed on a side facing the eye 200 of the first spectroscope 620, so as to implement the foregoing features.

It can be seen from FIG. 6, because in this implementation manner, the focusing point detector 600 is located on a side far away from the eye 200 of a lens of the glasses 400, when an optical parameter of the eye is calculated, the lens may also be considered as a part of the eye; in this case, an optical feature of the lens does not need to be known.

In other implementation manners of the embodiment of this application, the focusing point detector 600 may be located on a side near the eye 200 of a lens of the glasses 400; in this case, an optical parameter of the lens needs to be obtained in advance, and when a distance from a focusing point is calculated, an influence factor of the lens is considered.

The light emitted by the light source is reflected by the second spectroscope 650, projected by the focal-distance-adjustable lens 630, and reflected by the first spectroscope 620, then enters the eye of the user through the lens of the glasses 400, and finally reaches a retina on the fundus; the camera 610 takes an image of the fundus from a pupil of the eye 200 through a light path formed by the first spectroscope 620, the focal-distance-adjustable lens 630, and the second spectroscope 650.

Figure 7:
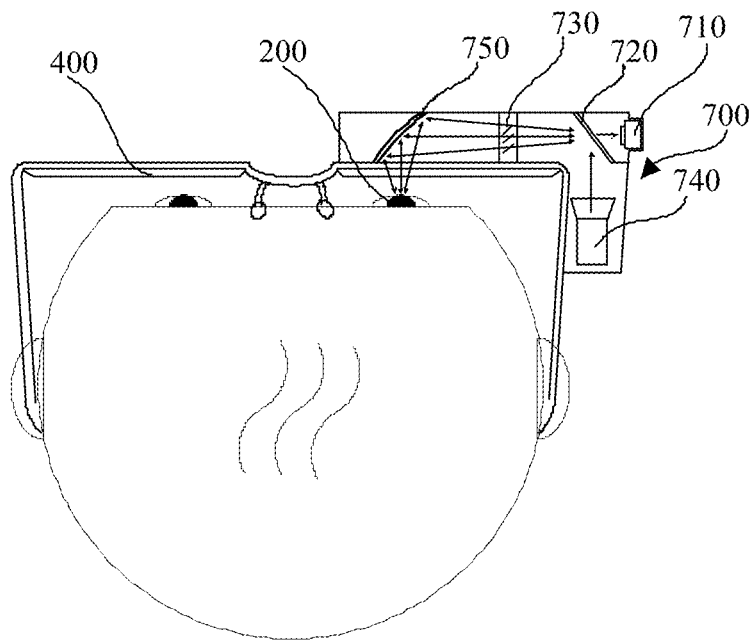
FIG. 7 is a schematic diagram of a focusing point detector, applied to glasses, of another vision protection imaging apparatus according to an embodiment of this application.

FIG. 7 is a schematic structural diagram of a focusing point detector 700 according to another implementation manner of the embodiment of this application. It can be seen from FIG. 7 that this implementation manner is similar to the implementation manner shown in FIG. 6, where the focusing point detector 700 comprises a micro camera 710, a second spectroscope 720, and a focal-distance-adjustable lens 730. A difference lies in that a projection apparatus 740 in this implementation manner is a projection apparatus 740 projecting a light spot pattern, and a curved-surface spectroscope 750 is used as a curved-surface beam splitting unit, to replace the first spectroscope in the implementation manner in FIG. 6.

The curved-surface spectroscope 750 is configured to transfer an image presented on a fundus to an image collection device separately corresponding to positions of a pupil when optical axis directions of an eye are different. In this way, the camera can take mixed overlapping images from various angles of an eyeball, but only an image of a part on the fundus that passes through the pupil can be formed clearly in the camera, and other parts are out of focus and therefore images of these parts cannot be formed clearly. Therefore, no serious interference to imaging of the part on the fundus is caused, and a feature of the part on the fundus can still be detected. Therefore, compared with the implementation manner shown in FIG. 6, in this implementation manner, an image on the fundus can be obtained very well when the eye gazes at different directions, so that the focusing point detector in this implementation manner has a wider application range and better detection accuracy.

Besides the foregoing implementation manner in which the adjustment triggering information is generated according to a result of determining whether the time during which the change amount of the distance between the gaze point of the eye and the eye is within the set range exceeds the set threshold, in a possible implementation manner of the embodiment of this application, the apparatus further comprises:

a regular triggering module, configured to regularly generate the adjustment triggering information according to a period, and send the adjustment triggering information to the parameter generating module.

Such a manner of regularly adjusting the imaging parameter of the adjustable lens module 110 has low costs and provides convenient adjustment, and therefore may be used as a complement to the foregoing manner in which adjustment is made after determining is performed, thereby further protecting vision of the user.

In order to affect use by the user as little as possible and exercise eyes of the user as effectively as possible, the parameter generating module generates the adjustment information of the imaging parameter of the adjustable lens module according to a preset adjustment criterion.

Preferably, in a possible implementation manner of the embodiment of this application, the adjustment criterion comprises:

repeatedly changing the imaging parameter of the adjustable lens module within a set adjustment range.

The set adjustment range may be set according to vision of a user (which may be average vision of ordinary users or may be specific vision of a current user), and it would be best that within the adjustment range, the user can still clearly or relatively clearly view the object by self-adjustment and by using the adjustable lens module. Most preferably, within the adjustment range, the user does not even notice that an imaging parameter of the optical system of the eye is being adjusted. Alternatively, in other possible implementation manners of the embodiment of this application, the vision of the user may not be considered, to directly let the user notice that the adjustable lens module is being adjusted and thereby exercise the eye in cooperation with the adjustment.

For example, the current imaging parameter of the adjustable lens module is used as a benchmark; a diopter of the adjustable lens module is first increased gradually and then decreased gradually to the benchmark; or the diopter may be decreased to a value less than the benchmark and then increased to the benchmark. Alternatively, the foregoing process may be further performed repeatedly, and extreme values to which the diopter is increased and decreased do not exceed the foregoing adjustment range.

In a possible implementation manner of the embodiment of this application, the adjustment criterion comprises:

adding a time-related additional value to a value of the imaging parameter of the adjustable lens module. In this implementation manner, preferably, the additional value is within an additional value range which is set.

For example, an additional value Delta is added to a current value of the focal distance, where Delta is a function of time t and is changed within a range of [−Min, +Max], that is, Delta=f(t), Delta∈[−Min, +Max]. By using the adjustment method in this implementation manner, the imaging parameter of the adjustable lens module can be adjusted continuously rather than changed abruptly, so that the user does not feel dizzy or have other uncomfortable feelings because of the adjustment.

Besides the foregoing adjustment method, in this application, the adjustment criterion of this application may also be formulated according to eye exercise methods for vision protection (for example, the Bates therapy) in ophthalmology researches.

Preferably, in a possible implementation manner of the embodiment of this application, the apparatus further comprises:

a user data obtaining module, configured to obtain data about a user.

Preferably, in a possible implementation manner of the embodiment of this application, the apparatus further comprises:

an adjustment criterion setting module, configured to set the adjustment criterion with reference to the data about the user.

The data about the user comprises one or more of the vision, age, gender, and occupation of the user and other information related to use of eyes. The data may be manually input by the user or another person, or may be automatically obtained by a collection analysis apparatus. For example, a communications module is disposed on the apparatus, and is configured to communicate with an external device (for example, a computer), and the user or another person may set the data about the user on the external device.

Certainly, besides the foregoing data about the user, the adjustment criterion or the like may also be set by using the external device. Preferably, the communications module is a wireless communications module. Certainly, a person skilled in the art may know that a wired communications module may also be used as the communications module in this application.

In other possible embodiments of this application, the adjustment criterion, the data about the user, and the like may all be set or obtained on the apparatus.

For each user, a specific adjustment criterion targeted at the user is set according to data about the user, which can improve a vision protection effect for the user. For example, in a possible implementation manner of the embodiment of this application, the user data obtaining module comprises a refractive correction unit, configured to study an imaging parameter, which is corresponding to the eye when the eye separately obtains expected images of an object at multiple distances, to obtain refractive correction information corresponding to the eye. The expected image may be, for example, a clear image or a relatively clear image of the object. The parameter generating module generates the adjustment information of the imaging parameter of the adjustable lens module according to the refractive correction information, so as to better adapt to use by different users and try not to affect work, life, and the like of a user.

Figure 8:
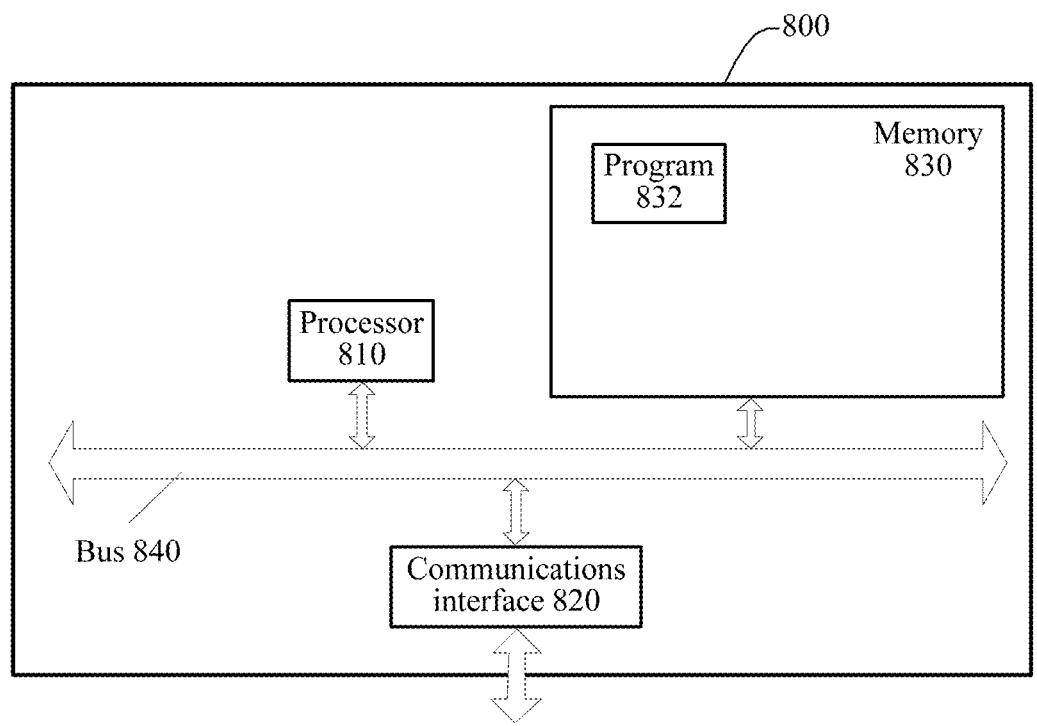
FIG. 8 is a structural block diagram of an information processing part of a vision protection imaging apparatus according to an embodiment of this application.

FIG. 8 is a schematic structural diagram of an information processing part 800 according to a possible implementation manner of an embodiment of this application. The specific embodiment of this application is not a limitation to specific implementation of the information processing part 800. As shown in FIG. 8, the information processing part 800 may comprise:

a processor 810, a communications interface 820, a memory 830, and a communications bus 840, where the processor 810, the communications interface 820, and the memory 830 communicate with each other through the communications bus 840.

The communications interface 820 is configured to communicate with a network element such as a client.

The processor 810 is configured to execute a program 832, and may specifically implement related functions of the analysis processing module and the parameter generating module in the specific implementation manners in FIG. 1 and FIG. 2*a* to FIG. 2*d*.

Specifically, the program 832 may comprise program code, where the program code comprises a computer operating instruction.

The processor 810 may be a central processing unit (CPU), an application specific integrated circuit (ASIC), or one or more integrated circuits configured to implement the embodiment of this application.

The memory 830 is configured to store the program 832. The memory 830 may comprise a high-speed RAM memory, and may further comprise a non-volatile memory, for example, at least one disk memory. The program 832 may specifically enable the information processing part to execute the following steps:

determining whether time during which a change amount of a distance between a gaze point of the eye and the eye is within a set range exceeds a set threshold, and when the time exceeds the set threshold, sending adjustment triggering information to a parameter generating module; and generating adjustment information of an imaging parameter of the adjustable lens module according to the adjustment triggering information.

For specific implementation of the steps in the program 832, reference may be made to the description of a corresponding step and unit in the embodiments of this application, which are not described herein again. A person skilled in the art may clearly understand that for the purpose of convenient and brief description, for a specific working process of the foregoing device and modules, reference may be made to the description of a corresponding process in the foregoing method embodiment, which is not described herein again.

Figure 9:
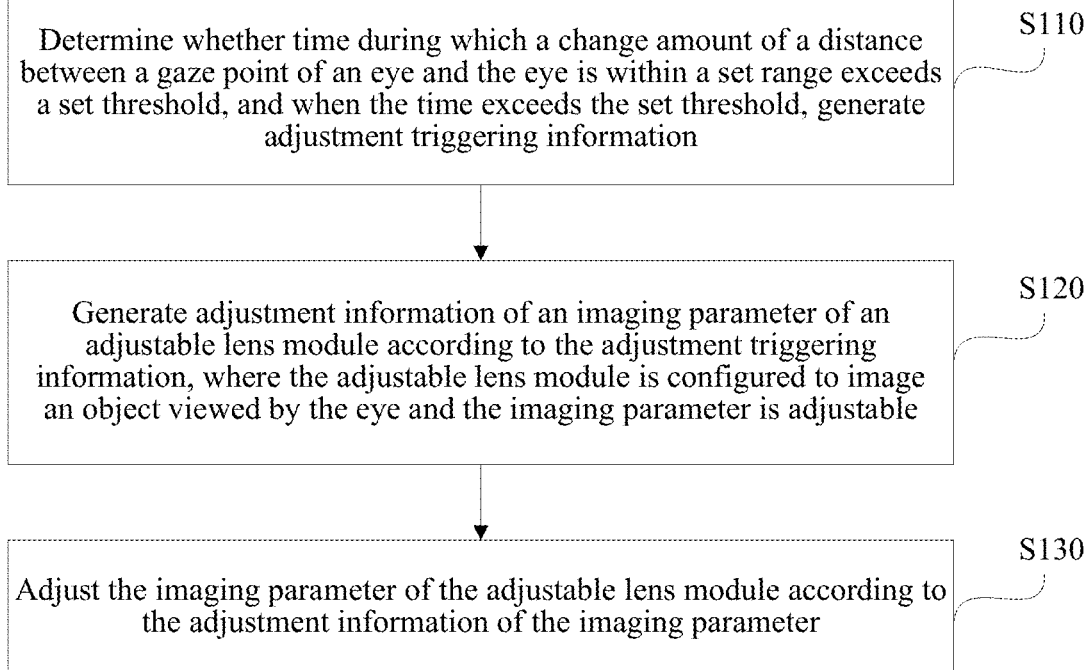
FIG. 9 is a flowchart of a vision protection imaging method according to an embodiment of this application.

As shown in FIG. 9, a possible implementation manner of an embodiment of this application provides a vision protection imaging method, comprising:

S110: Determine whether time during which a change amount of a distance between a gaze point of an eye and the eye is within a set range exceeds a set threshold, and when the time exceeds the set threshold, generate adjustment triggering information.

S120: Generate adjustment information of an imaging parameter of an adjustable lens module according to the adjustment triggering information, where the adjustable lens module is configured to image an object viewed by the eye and the imaging parameter is adjustable.

S130: Adjust the imaging parameter of the adjustable lens module according to the adjustment information of the imaging parameter.

Specific implementation manners of the foregoing steps in the embodiment of this application may be implemented according to corresponding description in the apparatus embodiment shown in FIG. 1, which is not described herein again.

In the method of this application, an image of an object is formed on a retina through the adjustable lens module and an optical system (comprising a crystalline lens) of an eye. In this application, it is determined whether time during which a change amount of a distance between a gaze point of the eye and the eye is within a set range exceeds a set threshold, so as to learn whether the eye is in a same state for a long time (especially a tension state for a long time when the eye views an object at a near distance), and when the eye is in a same state for a long time, an imaging parameter of the adjustable lens module is adjusted; in order to keep the image of the object obtained on the retina unchanged or basically unchanged, a brain controls the optical system of the eye to be adjusted accordingly as well, thereby exercising the eye. In this way, a probability of occurrence or deterioration of a sight problem such as nearsightedness due to improper use of eyes is reduced without affecting work, study, entertainment, or the like being currently performed by a user.

The method in this embodiment may be applied to an apparatus that is easy to carry and convenient to use, for example, glasses (comprising frame glasses, contact lenses, goggles, or the like). Especially for a user who has a sight problem such as a refractive error and therefore needs to wear refractive correction glasses, the apparatus in this application can be directly implemented on the refractive correction glasses, so as to reduce a probability that the sight problem of the user further deteriorates or reduce a deterioration degree of the sight problem of the user while correcting vision of the user or even mitigate the sight problem such as the refractive error of the user. In this case, the user does not need an additional device to protect an eye, and therefore no extra burden is brought to the work, life, or the like of the user.

Certainly, in other possible implementation manners of the embodiment of this application, the vision protection imaging apparatus may also be, for example, another optical device used in cooperation with eyes of a user, such as a helmet eye shield, a front windshield of a cab, or a microscope.

Preferably, in a possible implementation manner of the embodiment of this application, the imaging parameter of the adjustable lens module comprises: a focal distance of the adjustable lens module.

Preferably, in a possible implementation manner of the embodiment of this application, the imaging parameter of the adjustable lens module comprises: an optical axis direction of the adjustable lens module.

In this application, whether the time during which the change amount of the distance between the gaze point of the eye and the eye is within the set range exceeds the set threshold may be determined in multiple manners, which comprise the following.

Preferably, in a possible implementation manner of the embodiment of this application, before step S110, the method further comprises:

collecting an image of a scene viewed by the eye.

Preferably, in a possible implementation manner of the embodiment of this application, the step S110, that is, the step of determining whether time during which a change amount of a distance between a gaze point of an eye and the eye is within a set range exceeds a set threshold comprises:

determining whether time during which a change amount of the image is within a set range exceeds the set threshold.

Preferably, in a possible implementation manner of the embodiment of this application, the step S110, that is, the step of determining whether time during which a change amount of a distance between a gaze point of an eye and the eye is within a set range exceeds a set threshold comprises:

determining, according to the image, whether the scene comprises an object having a presetted feature, and when the scene comprises an object having a presetted feature, determining whether time during which the scene comprises the object having the presetted feature exceeds the set threshold.

Preferably, in a possible implementation manner of the embodiment of this application, the feature comprises one or more of features such as a shape, a material, a texture, and brightness.

Preferably, in a possible implementation manner of the embodiment of this application, before step S110, the method further comprises:

collecting depth information of a scene viewed by the eye.

Preferably, in a possible implementation manner of the embodiment of this application, the step S110, that is, the step of determining whether time during which a change amount of a distance between a gaze point of an eye and the eye is within a set range exceeds a set threshold comprises:

determining whether time during which a change amount of the depth information is within a set range exceeds the set threshold.

Preferably, in a possible implementation manner of the embodiment of this application, the step S110, that is, the step of determining whether time during which a change amount of a distance between a gaze point of an eye and the eye is within a set range exceeds a set threshold comprises:

determining, according to the depth information of the scene, whether the scene comprises an object having a presetted feature, and when the scene comprises an object having a presetted feature, determining whether time during which the scene comprises the object having the presetted feature exceeds the set threshold.

Preferably, in a possible implementation manner of the embodiment of this application, the feature comprises a shape of the object.

Preferably, in a possible implementation manner of the embodiment of this application, before step S110, the method further comprises:

collecting posture information of the head of a user.

Preferably, in a possible implementation manner of the embodiment of this application, the step S110, that is, the step of determining whether time during which a change amount of a distance between a gaze point of an eye and the eye is within a set range exceeds a set threshold comprises:

determining, according to the posture information, whether time during which a change amount of a posture of the head of the user is within a set range exceeds the set threshold.

Preferably, in a possible implementation manner of the embodiment of this application, before step S110, the method further comprises:

obtaining a position of a focusing point of a sight line of the eye.

Preferably, in a possible implementation manner of the embodiment of this application, the step S110, that is, the step of determining whether time during which a change amount of a distance between a gaze point of an eye and the eye is within a set range exceeds a set threshold comprises:

determining whether time during which a change amount of the position of the focusing point is within a set range exceeds the set threshold.

Preferably, in a possible implementation manner of the embodiment of this application, the step of obtaining a position of a focusing point of a sight line of the eye comprises:

collecting an image presented on a fundus of the eye;

adjusting an imaging parameter of a light path between the eye and a collection position to collect a clearest image; and processing the collected image, calculating the position of the focusing point of the eye according to the imaging parameter of the light path between the eye and the collection position and an optical parameter of the eye when the clearest image is obtained.

Preferably, in a possible implementation manner of the embodiment of this application, the optical parameter of the eye comprises an optical axis direction of the eye.

Preferably, in a possible implementation manner of the embodiment of this application, the adjusting an imaging parameter of a light path between the eye and a collection position comprises:

adjusting a focal distance and/or a position of an optical device on the light path between the eye and the collection position.

Preferably, in a possible implementation manner of the embodiment of this application, the adjusting an imaging parameter of a light path between the eye and a collection position to collect a clearest image comprises:

transferring the image presented on the fundus to the collection position separately corresponding to positions of a pupil when optical axis directions of the eye are different.

Preferably, in a possible implementation manner of the embodiment of this application, the method further comprises:

projecting a light spot pattern onto the fundus.

Preferably, in a possible implementation manner of the embodiment of this application, the step S110 comprises:

when the change amount of the distance between the gaze point of the eye and the eye exceeds the set range or after adjustment of the imaging parameter of the adjustable lens module is completed, re-counting time.

Preferably, in a possible implementation manner of the embodiment of this application, the method further comprises:

regularly generating the adjustment triggering information according to a period.

Preferably, in a possible implementation manner of the embodiment of this application, in this method, the adjustment information of the imaging parameter of the adjustable lens module is generated according to a preset adjustment criterion.

Preferably, in a possible implementation manner of the embodiment of this application, the adjustment criterion comprises:

repeatedly changing the imaging parameter of the adjustable lens module within a set adjustment range.

Preferably, in a possible implementation manner of the embodiment of this application, the adjustment criterion comprises:

adding a time-related additional value to a value of the imaging parameter of the adjustable lens module.

Preferably, in a possible implementation manner of the embodiment of this application, the additional value is within a set additional value range.

Preferably, in a possible implementation manner of the embodiment of this application, the method further comprises:

obtaining data about a user.

Preferably, in a possible implementation manner of the embodiment of this application, the adjustment criterion is set with reference to the data about the user.

Specific implementation manners of the foregoing steps may be implemented according to corresponding description in the foregoing apparatus embodiment, which is not described herein again.

A person skilled in the art may understand that in the foregoing method in the specific implementation manners of this application, the serial numbers of the steps do not indicate an execution sequential order; a sequential order in which the steps are executed should be determined according to functions and internal logic of the steps, and the serial numbers should not constitute any limitation to an implementation process of the specific implementation manners of this application.

A person of ordinary skill in the art may be aware that, in combination with the examples described in the embodiments disclosed in this specification, units and method steps may be implemented by electronic hardware or a combination of computer software and electronic hardware. Whether the functions are performed by hardware or software depends on particular applications and design constraint conditions of the technical solutions. A person skilled in the art may use different methods to implement the described functions for each particular application, but such implementation should not be considered beyond the scope of this application.

When implemented in a form of a software functional unit and sold or used as an independent product, the functions may be stored in a computer-readable storage medium. Based on such an understanding, the technical solutions of this application essentially, or the part contributing to the prior art, or a part of the technical solutions may be implemented in a form of a software product. The computer software product is stored in a storage medium and comprises several instructions for instructing a computer device (which may be a personal computer, a server, a network device, or the like) to perform all or a part of the steps of the methods described in the embodiments of this application. The foregoing storage medium comprises: any mediums capable of storing program code, such as a USB flash drive, a removable hard disk, a read-only memory (ROM), a random access memory (RAM), a magnetic disk, or an optical disc.

The foregoing implementation manners are merely intended for describing this application rather than limiting this application. A person of ordinary skill in the art may make various variations or modifications without departing from the spirit and scope of this application. Therefore, all equivalent technical solutions also fall within the scope of this application, and the patent protection scope of this application shall be limited by the claims.

What is claimed is:

1. An apparatus, comprising:
an adjustable lens module, comprising at least one lens, configured to image an object determined to be viewed by an eye;
a processor; and
a memory that stores executable instructions that, when executed by the processor, facilitate performance of operations, comprising:
determining whether a time, during which a change amount of a distance between a gaze point of the eye and the eye is within a set range, exceeds a set threshold, and, in response to the time being determined to exceed the set threshold, sending adjustment triggering information;

in response to receiving the adjustment triggering information, generating, by the apparatus, adjustment information of at least one imaging parameter of the adjustable lens module according to the adjustment triggering information; and initiating adjusting of the at least one imaging parameter of the adjustable lens module according to the adjustment information of the at least one imaging parameter, so that a brain controls an optical system of the eye, resulting in keeping the image of the object on a retina of the eye unchanged, wherein the at least one imaging parameter is related to exercising of the eye.

2. The apparatus of claim 1, further comprising:
an image sensor configured to collect multiple images according to a time order of a scene determined to be viewed by the eye.

3. The apparatus of claim 2, wherein the operations further comprise:
determining whether another time, during which another change amount of the multiple images is within another set range, exceeds the set threshold.

4. The apparatus of claim 2, wherein the operations further comprise:
determining, according to the multiple images, whether the scene comprises another object having at least one preset feature, and in response to the scene being determined to comprise the other object, determining whether another time, during which the scene comprises the object exceeds the set threshold.

5. The apparatus of claim 1, further comprising:
a depth sensor configured to collect depth information of a scene determined to be viewed by the eye.

6. The apparatus of claim 5, wherein the operations further comprise:
determining whether another time, during which another change amount of the depth information is within a set range, exceeds the set threshold.

7. The apparatus of claim 5, wherein the operations further comprise:
determining, according to the depth information of the scene, whether the scene comprises another object having at least one preset feature, and in response to the scene being determined to comprise the other object, determine whether another time, during which the scene comprises the other object, exceeds the set threshold.

8. The apparatus of claim 1, further comprises:
a motion posture sensor configured to collect posture information of a head of a user.

9. The apparatus of claim 8, wherein the operations further comprise:
determining, according to the posture information, whether another time, during which another change amount of a posture of the head of the user is within a set range, exceeds the set threshold.

10. The apparatus of claim 1, further comprising:
a focusing point detector configured to obtain a position of a focusing point of a sight line of the eye.

11. The apparatus of claim 10, wherein the operations further comprise:
determining whether another time, during which another change amount of the position of the focusing point is within a set range, exceeds the set threshold.

12. The apparatus of claim 10, wherein the focusing point detector comprises:
an image collection device configured to collect at least one image presented on a fundus of the eye;
an adjustable imaging device configured to adjust at least one other imaging parameter of a light path between the eye and the image collection device, wherein the image collection device obtains a clearest image; and
the focusing point detector processes the at least one image, according to the at least one other imaging parameter and at least one optical parameter of the eye corresponded to the clearest image, to obtain the position of the focusing point of the eye.

13. The apparatus of claim 12, wherein the adjustable imaging device comprises:
an adjustable lens unit located on the light path between the eye and the image collection device, wherein a focal distance of the adjustable lens unit is adjustable, or at least one position of the adjustable lens unit on the light path is adjustable.

14. The apparatus of claim 12, wherein the adjustable imaging device comprises:
a curved-surface beam splitting unit configured to transfer, to the image collection device, the at least one image presented on the fundus corresponding to different positions of a pupil in response to different optical axis directions of the eye.

15. The apparatus of claim 12, wherein the focusing point detector further comprises:
a projection device configured to project a light spot pattern onto the fundus.

16. The apparatus of claim 1, wherein the operations further comprise:
a timing unit configured to count time, and in response to the change amount of the distance being determined to exceed the set range or the adjustment of the at least one imaging parameter being determined to have completed, re-count the time.

17. The apparatus of claim 1, wherein the at least one imaging parameter comprises:
a focal distance of the adjustable lens module.

18. The apparatus of claim 1, wherein the at least one imaging parameter comprises:
an optical axis direction of the adjustable lens module.

19. The apparatus of claim 1, the operations further comprising:
triggering the generating of the adjustment information according to a period.

20. The apparatus of claim 1, wherein the operations further comprise:
generating the adjustment information of the adjustable lens module according to a preset adjustment criterion.

21. The apparatus of claim 20, wherein the operations further comprise:
obtaining data about a user.

22. The apparatus of claim 21, wherein the operations further comprise:
setting the adjustment criterion with reference to the data about the user.

23. The apparatus of claim 1, wherein the apparatus is a pair of glasses.

24. A method, comprising:
determining, by a system comprising a processor, whether a time, during which a change amount of a distance between a gaze point of an eye and the eye is within a set range exceeds a set threshold, and in response to the time being determined to exceed the set threshold, generating adjustment triggering information;

generating adjustment information of at least one imaging parameter of an adjustable lens module according to the adjustment triggering information, wherein the adjustable lens module is configured to image an object determined to be viewed by the eye; and adjusting the at least one imaging parameter of the adjustable lens module according to the adjustment information of the at least one imaging parameter, so that a brain controls an optical system of the eye, resulting in keeping the image of the object on a retina of the eye unchanged, wherein the at least one imaging parameter relates to exercising of the eye.

25. The method of claim 24, further comprising:
collecting multiple images according to time order of a scene determined to be viewed by the eye.

26. The method of claim 25, wherein the determining whether the time exceeds the set threshold comprises:
determining whether another time, during which another change amount of the multiple images is within a set range, exceeds the set threshold.

27. The method of claim 25, wherein the determining whether the time exceeds the set threshold comprises:
determining, according to the multiple images, whether the scene comprises another object having at least one predefined feature, and, in response to the scene being determined to comprise the other object, determining whether another time, during which the scene comprises the object having the predefined feature, exceeds the set threshold.

28. The method of claim 27, wherein the feature comprises at least one of a shape, a material, a texture, or a brightness.

29. The method of claim 24, further comprising:
collecting depth information of a scene determined to be viewed by the eye.

30. The method of claim 29, wherein the determining whether the time exceeds the set threshold comprises:
determining whether another time, during which another change amount of the depth information is within a set range, exceeds the set threshold.

31. The method of claim 29, wherein the determining whether the time exceeds the set threshold comprises:
determining, according to the depth information of the scene, whether the scene comprises another object having at least one predefined feature, and, in response to the scene being determined to comprise the other object, determining whether another time, during which the scene comprises the object having the predefined feature, exceeds the set threshold.

32. The method of claim 31, wherein the feature comprises a shape of the other object.

33. The method of claim 24, further comprising:
collecting posture information of a head of a user.

34. The method of claim 33, wherein the determining whether the time exceeds the set threshold comprises:
determining, according to the posture information, whether another time, during which another change amount of a posture of the head of the user is within a set range, exceeds the set threshold.

35. The method of claim 24, further comprising:
obtaining a position of a focusing point of a sight line of the eye.

36. The method of claim 35, wherein the determining whether the time exceeds the set threshold comprises:
determining whether another time, during which another change amount of the position of the focusing point is within a set range, exceeds the set threshold.

37. The method of claim 35, wherein the obtaining the position of the focusing point of the sight line of the eye comprises:
collecting at least one image presented on a fundus of the eye;
adjusting at least one other imaging parameter of a light path between the eye and a collection position of the at least one image to obtain a clearest image; and
processing the at least one image, according to the at least one other imaging parameter and at least one optical parameter of the eye corresponded to the clearest image, to obtain the position of the focusing point of the eye.

38. The method of claim 37, wherein the optical parameter of the eye comprises an optical axis direction of the eye.

39. The method of claim 37, wherein the adjusting the at least one other imaging parameter of the light path between the eye and the collection position comprises:
adjusting a position of at least one optical device on the light path between the eye and the collection position, or a focal distance of the at least one optical device.

40. The method of claim 37, wherein the adjusting the at least one other imaging parameter of the light path between the eye and the collection position to collect the clearest image comprises:
transferring, to the collection position, the at least one image presented on the fundus corresponding to different positions of a pupil in response to different optical axis directions of the eye.

41. The method of claim 37, further comprising:
projecting a light spot pattern onto the fundus.

42. The method of claim 24, wherein the determining whether the time exceeds the set threshold comprises:
in response to the change amount of the distance between the gaze point of the eye and the eye being determined to exceed the set range or the adjustment of the at least one imaging parameter of the adjustable lens module being determined to be completed, re-counting time.

43. The method of claim 24, wherein the at least one imaging parameter of the adjustable lens module comprises:
a focal distance of the adjustable lens module.

44. The method of claim 24, wherein the at least one imaging parameter of the adjustable lens module comprises:
an optical axis direction of the adjustable lens module.

45. The method of claim 24, further comprising:
generating the adjustment triggering information according to a period.

46. The method of claim 24, wherein the generating the adjustment information of the at least one imaging parameter of the adjustable lens module comprises:
determining the adjustment information of the at least one imaging parameter of the adjustable lens module by an adjustment criterion preset.

47. The method of claim 46, wherein the adjustment criterion comprises:
repeatedly changing the at least one imaging parameter of the adjustable lens module within a set adjustment range.

48. The method of claim 46, wherein the adjustment criterion comprises:

adding a time-related additional value to a value of the at least one imaging parameter of the adjustable lens module.

49. The method of claim 46, further comprising:
obtaining data about a user.

50. The method of claim 49, further comprising:
setting the adjustment criterion with reference to the data about the user.

51. A computer readable storage device comprising executable instructions that, in response to execution, cause a system comprising a processor to perform operations, comprising:
  determining whether a time, during which a change in a distance between a gaze point of an eye and the eye is within a defined range, exceeds a threshold value, and, in response to the time being determined to exceed the threshold value, generating adjustment triggering information;
  generating adjustment information for an imaging parameter of an adjustable lens module according to the adjustment triggering information, wherein the adjustable lens module images an object determined to be viewed by the eye; and
  adjusting the imaging parameter of the adjustable lens module according to the adjustment information of the imaging parameter, so that a brain controls an optical system of the eye, resulting in keeping the image of the object on a retina of the eye unchanged, wherein the at least one imaging parameter corresponds to exercising of the eye.

* * * * *